US012648868B2

(12) United States Patent (10) Patent No.: US 12,648,868 B2
Springman et al. (45) Date of Patent: Jun. 9, 2026

(54) ANKLE FOOT ORTHOSIS WITH TRACK SYSTEM AND MECHANISM

(71) Applicant: Thrive Orthopedics, LLC, Carmel, IN (US)

(72) Inventors: Michael Springman, Carmel, IN (US); Joseph Deheer, Carmel, IN (US)

(73) Assignee: Thrive Orthopedics, LLC

( * ) Notice: Subject to any disclaimer, the term of this patent is extended or adjusted under 35 U.S.C. 154(b) by 18 days.

(21) Appl. No.: 18/731,227

(22) Filed: May 31, 2024

(65) Prior Publication Data
US 2024/0398598 A1 Dec. 5, 2024

Related U.S. Application Data

(63) Continuation-in-part of application No. PCT/US2023/072177, filed on Aug. 14, 2023.

(60) Provisional application No. 63/397,464, filed on Aug. 12, 2022.

(51) Int. Cl.
*A61F 5/01* (2006.01)

(52) U.S. Cl.
CPC .......... *A61F 5/0127* (2013.01); *A61F 5/0123* (2013.01); *A61F 2005/0158* (2013.01); *A61F 2005/0174* (2013.01)

(58) Field of Classification Search
CPC .... A61F 5/0113; A61F 5/0111; A61F 5/0127; A61F 2005/0158; A61F 5/0195; A61F 5/0585; A43B 7/20
See application file for complete search history.

(56) References Cited

U.S. PATENT DOCUMENTS

| | | | |
|---|---|---|---|
| 6,383,156 B1 * | 5/2002 | Enzerink | A61F 5/0125 |
| | | | 602/26 |
| 7,125,392 B2 | 10/2006 | Scott | |
| 9,180,037 B1 * | 11/2015 | Smith | A61F 5/0111 |
| 9,591,895 B2 | 3/2017 | Shirai | |
| 11,253,383 B2 | 2/2022 | Hanft | |
| 11,717,431 B2 | 8/2023 | Romo et al. | |
| 2016/0213506 A1 * | 7/2016 | Chen | A61F 5/30 |
| 2020/0375776 A1 * | 12/2020 | Thor | A61F 5/0111 |
| 2023/0201018 A1 | 6/2023 | Raimondo et al. | |

FOREIGN PATENT DOCUMENTS

EP 4555979 A1 * 5/2025 ........... A61F 5/0127

* cited by examiner

*Primary Examiner* — Kari K Rodriquez
(74) *Attorney, Agent, or Firm* — Gutwein Law; Tyler Droste

(57) ABSTRACT

An orthosis device that can include a strut member, a housing member, a cuff member, and a locking mechanism. The strut member can have an extension portion and footplate portion. The strut member can include a track portion extending along a first side of the extension portion. The track portion can extend a pre-determined distance along the extension portion. The extension portion can extend in a first direction generally perpendicular from the footplate portion. A portion of the strut member can pass through a cavity in the housing member and allow for the adjustability of the height of the housing member along the extension portion. The locking mechanism can engage the track portion to lock the housing member at various positions along the track as desired by the user. The orthosis device can include a secondary housing member to provide additional support component for a user.

8 Claims, 26 Drawing Sheets

1

ANKLE FOOT ORTHOSIS WITH TRACK SYSTEM AND MECHANISM

CROSS-REFERENCE TO RELATED APPLICATION

This patent application is a continuation-in-part application that claims priority PCT/US23/72177 filed on Aug. 14, 2023, which claims priority to Provisional Application 63/397,464 filed Aug. 12, 2022, the disclosure of which is considered part of the disclosure of this application and is hereby incorporated by reference in its entirety.

FIELD OF THE INVENTION

This invention relates generally to an ankle foot orthosis device and method thereof.

BACKGROUND

An Ankle Foot Orthosis (AFO), is commonly used device to improve walking patterns by reducing, preventing or limiting movement of the lower leg and foot and by supporting weak muscles. In order to maximize function and patient comfort, a medical professional typically fits the patient with a prefabricated or custom ankle foot orthosis that has a footplate, strut, and leg cuff that appropriately accommodate the patient's anatomy.

Although custom-made AFOs can be manufactured to achieve a specific and appropriate cuff height for patients, traditional prefabricated AFOs come in a limited number (typically 4-5 sizes per style) of height options, limiting the effectiveness and comfort of these devices in relation to the patient's specific anatomical needs. Universal size, height-adjustable prefabricated AFOs do allow for height adjustments mimicking traditional prefabricated AFO heights but current designs in the market only allow adjustability to a limited number of fixed heights (typically 4-5) that correspond to predetermined positions or holes in the strut and leg cuff that may require manual assembly with hardware, screws, nuts, bolts, and tools and still do little to remedy the limited height options for users. There exists a need for an improved orthosis device that allows for a wide range of adjustability to accommodate users of various heights, thereby by increasing the effectiveness of the orthosis while minimizing the time it takes to assembly the orthosis device.

It is an object of the present invention to provide an improvement on current AFO designs by substantially increasing the number of possible height-adjustable cuff placement positions and eliminating the need for assembly, hardware, screws, nuts, bolts, or tools to make such height adjustments.

BRIEF SUMMARY OF THE INVENTION

In one aspect, this disclosure is related to an orthosis device having an adjustable track portion and locking mechanism.

In another aspect, this disclosure is a related to a method of providing an adjustable orthosis device to easily accommodate different sized users.

In another aspect, this disclosure is related to an orthosis device that can include a strut member, a housing member, a cuff member, and a locking mechanism. The strut member can have an extension portion and footplate portion. The strut member can include a track portion extending along a first side of the extension portion. The track portion can extend a pre-determined distance along the extension portion. The extension portion can extend in a first direction generally perpendicular from the footplate portion. The footplate portion can be configured to accommodate a user's foot. A housing member be configured to house a portion of the extension portion of the strut member and allow the housing member to move from a first position along the track portion to a second position along the track portion. The adjustable cuff member can be removably coupled to the housing member and can include a padded portion and a fastening band. The locking mechanism can be removably coupled or permanently affixed to the housing the housing member and can be configured to interface with the track portion to lock the housing member at one or more positions along the track portion.

In another aspect, the present disclosure is related to an orthosis device comprising a strut member, a housing member, an adjustable cuff or brace member, and a locking mechanism. The strut member can have an extension portion and footplate portion, wherein the strut member includes a track portion extending along a first side of the extension portion. The extension portion can extend up generally perpendicular from the footplate portion. The housing member can have a cavity formed therethrough configured to house a portion of the extension portion of the strut member. The housing member can move from a first position along the track portion to a second position along the track portion. The housing portion can also house a portion of the track portion. The adjustable cuff member or brace member can include a cuff or brace component. The brace component can be part of a larger brace system such as a knee brace. The adjustable cuff member includes a padded portion and a fastening band. The locking mechanism can be coupled to the housing member and configured to interface with the track portion to lock the housing member at one or more positions along the track portion. The orthosis device can further include a secondary support member that can be removably coupled to the track portion. The secondary support member can include a housing portion and a locking mechanism to lock the secondary support member in place along the track portion. The secondary support member can additionally include a flange portion that can be coupled to or incorporated as part of the housing member.

In another aspect, the present disclosure is related to an ankle foot orthosis device comprising a strut member, a housing member, and adjustable cuff member, and a locking mechanism. The strut member can have an extension portion and footplate portion. The strut member can include a track portion extending along a first side of the extension portion, wherein the extension portion extends up generally perpendicular from the footplate portion. The housing member can have an interior cavity formed therethrough configured to house a portion of the extension portion of the strut member. The housing member can similarly house a portion of the track portion. The housing member can move from a first position along the track portion to a second position along the track portion. The adjustable cuff member can include a padded portion and a fastening band. The locking mechanism can be coupled to the housing member. A portion of the locking mechanism can interface with the track portion to lock the housing member at one or more positions along the track portion. The locking mechanism can include a first surface, a second surface, a first side, second side, a third side, and a fourth side, wherein a first coupling member is formed along the third side and a second coupling member is formed along the third side, wherein the first coupling member and second coupling member are configured to interface with the housing member. The locking mechanism can be removably couplable to the housing member and have one or more interfacing members configured to interface and engage with one or more corresponding engagement members to maintain the housing member in a desired location along the track portion. The locking mechanism can further include one or more locating members that interface with one or more locating apertures on the housing member to properly position the locking mechanism onto the housing member.

The invention now will be described more fully hereinafter with reference to the accompanying drawings, which are intended to be read in conjunction with both this summary, the detailed description and any preferred and/or particular embodiments specifically discussed or otherwise disclosed. This invention may, however, be embodied in many different forms and should not be construed as limited to the embodiments set forth herein; rather, these embodiments are provided by way of illustration only and so that this disclosure will be thorough, complete and will fully convey the full scope of the invention to those skilled in the art.

DETAILED DESCRIPTION OF THE INVENTION

Figure 1A:
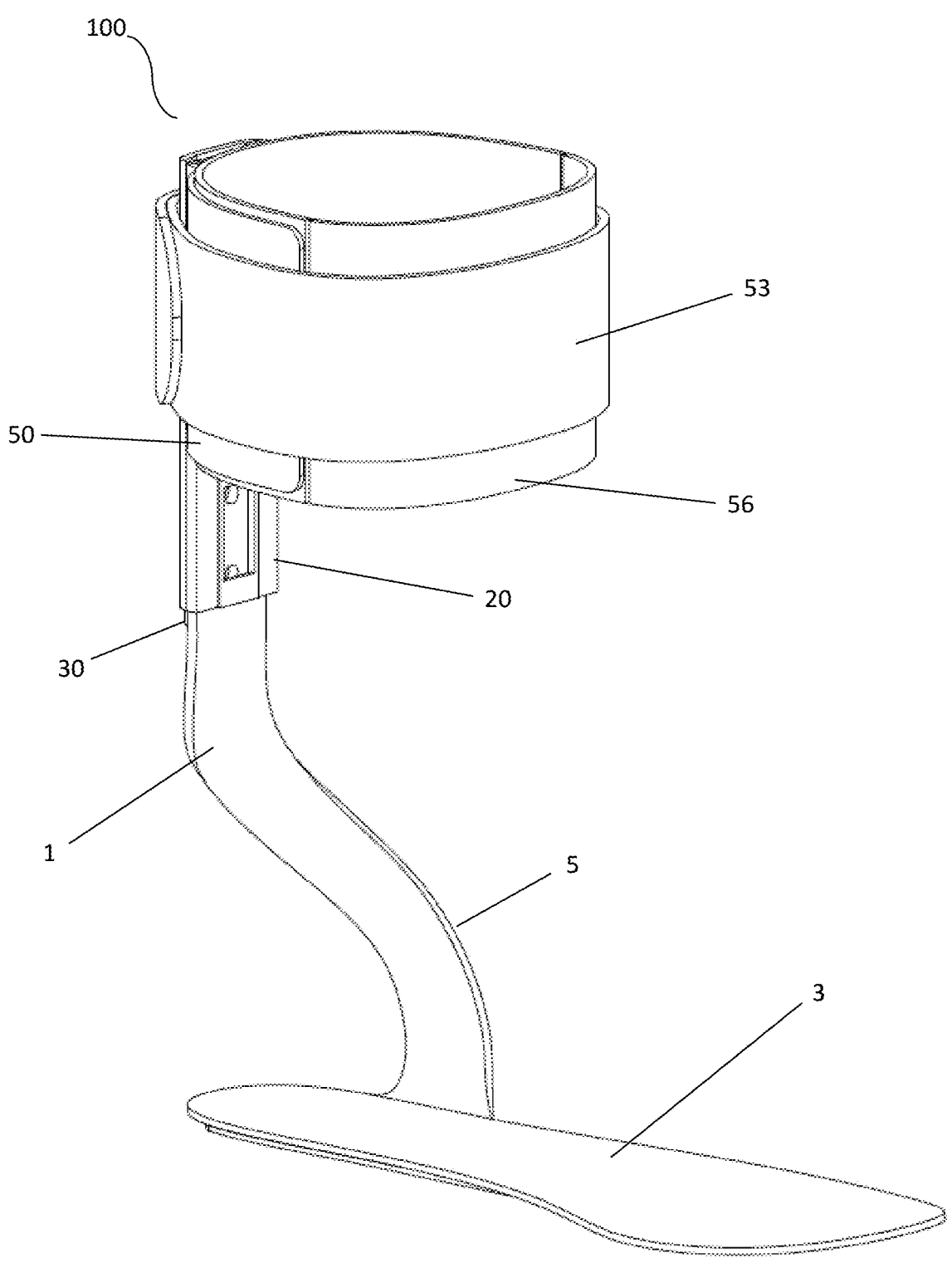
FIG. 1A is an illustration of a front perspective view of an exemplary embodiment of an orthosis device of the present disclosure in a retracted position.

The following detailed description includes references to the accompanying drawings, which forms a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, and logical changes may be made without departing from the scope of the present invention. The following detailed description is, therefore, not to be taken in a limiting sense.

Before the present invention of this disclosure is described in such detail, however, it is to be understood that this invention is not limited to particular variations set forth and may, of course, vary. Various changes may be made to the invention described and equivalents may be substituted without departing from the true spirit and scope of the invention. In addition, many modifications may be made to adapt a particular situation, material, composition of matter, process, process act(s) or step(s), to the objective(s), spirit or scope of the present invention. All such modifications are intended to be within the scope of the disclosure made herein.

Unless otherwise indicated, the words and phrases presented in this document have their ordinary meanings to one of skill in the art. Such ordinary meanings can be obtained by reference to their use in art and by reference to general and scientific dictionaries.

References in the specification to "one embodiment" indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The following explanations of certain terms are meant to be illustrative rather than exhaustive. These terms have their ordinary meanings given by usage in the art and in addition include the following explanations.

As used herein, the term "and/or" refers to any one of the items, any combination of the items, or all of the items with which this term is associated.

As used herein, the singular forms "a," "an," and "the" include plural reference unless the context clearly dictates otherwise.

As used herein, the terms "include," "for example," "such as," and the like are used illustratively and are not intended to limit the present invention.

As used herein, the terms "preferred" and "preferably" refer to embodiments of the invention that may afford certain benefits, under certain circumstances. However, other embodiments may also be preferred, under the same or other circumstances.

Furthermore, the recitation of one or more preferred embodiments does not imply that other embodiments are not useful and is not intended to exclude other embodiments from the scope of the invention.

As used herein, the term "coupled" means the joining of two members directly or indirectly to one another. Such joining may be stationary in nature or movable in nature. Such joining may be achieved with the two members, or the two members and any additional intermediate members being integrally formed as a single unitary body with one another or with the two members or the two members and any additional intermediate members being attached to one another. Such joining may be permanent in nature or alternatively may be removable or releasable in nature. Similarly, coupled can refer to a two member or elements being in communicatively coupled, wherein the two elements may be electronically, through various means, such as a metallic wire, wireless network, optical fiber, or other medium and methods.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element without departing from the teachings of the disclosure.

6

Figure 1B:
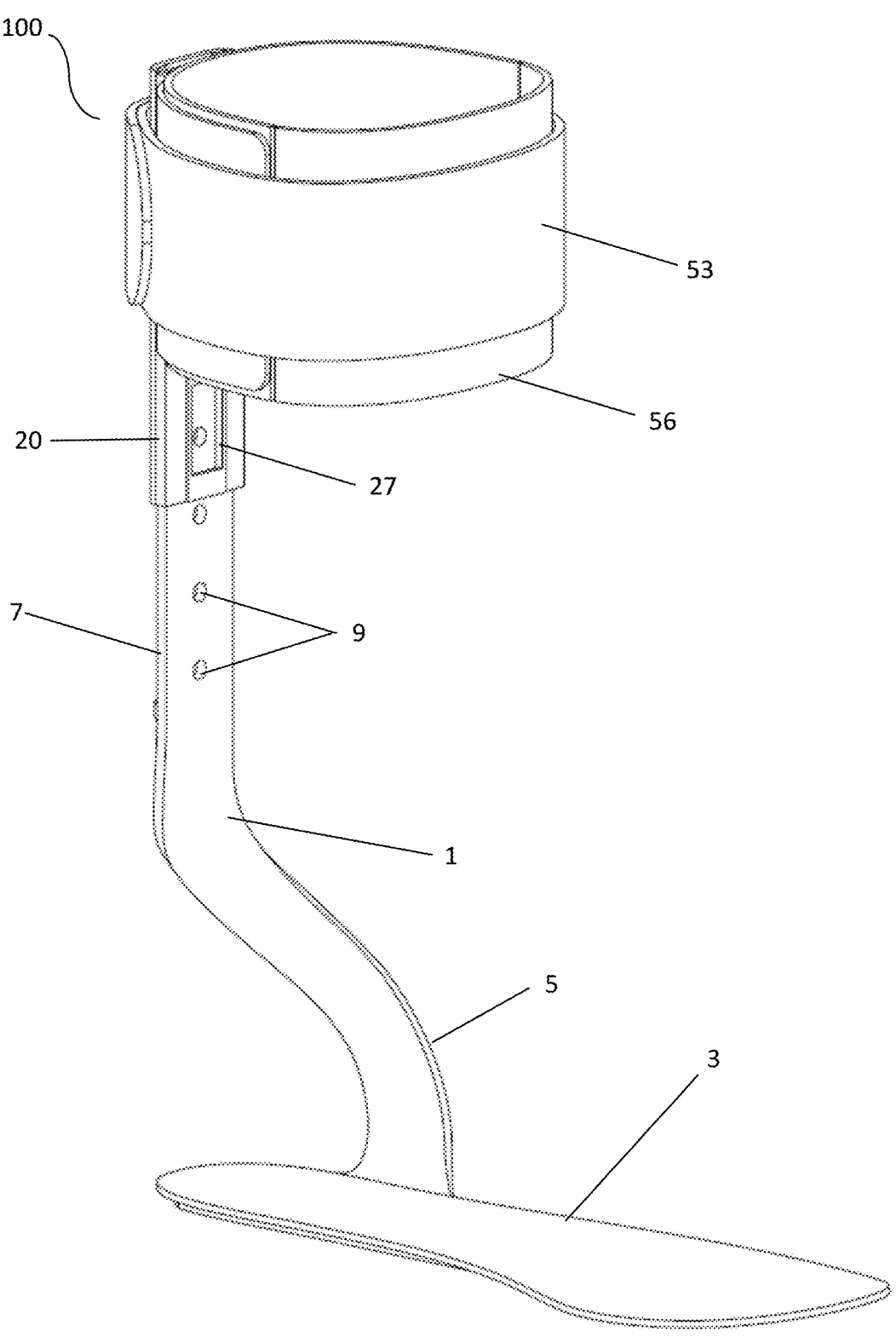
FIG. 1B is an illustration of a front perspective view of an exemplary embodiment of an orthosis device of the present disclosure in an extended position.

Referring now to the FIGS. 1A-B, the present disclosure provides an adjustable orthosis device 100 having a strut member 1 that can include a footplate portion 3, a curved portion 5, and an extension portion 7. The curved portion 5 can be configured to approximate a user's ankle region so as to provide room to prevent rubbing or irritation. The extension portion 7 can have one or more apertures 9 to allow for coupling of various other components to the strut member 1. The apertures 9 can be formed on an extension portion 7 of the strut member 1. At least a portion of the extension portion 7 can be housed within a housing member 20. The apertures 9 in the extension portion 7 can also be used as a coupling means for removably coupling a track portion 40 to the extension portion 7 of the strut member 1. The housing member 20 can have a first side 21 and a second side 23 and a cavity 25 formed through the length of the housing member 20. In some exemplary embodiments, the housing member 20 can include a locking mechanism 30 on a first side and a channel 27 formed along a portion of the second side. A locking mechanism 30 can be removably coupled to the housing member 20 and fit with in an aperture 29 on the first side of the housing member 20 or can alternatively be formed as part of the housing member 20.

Figure 4:
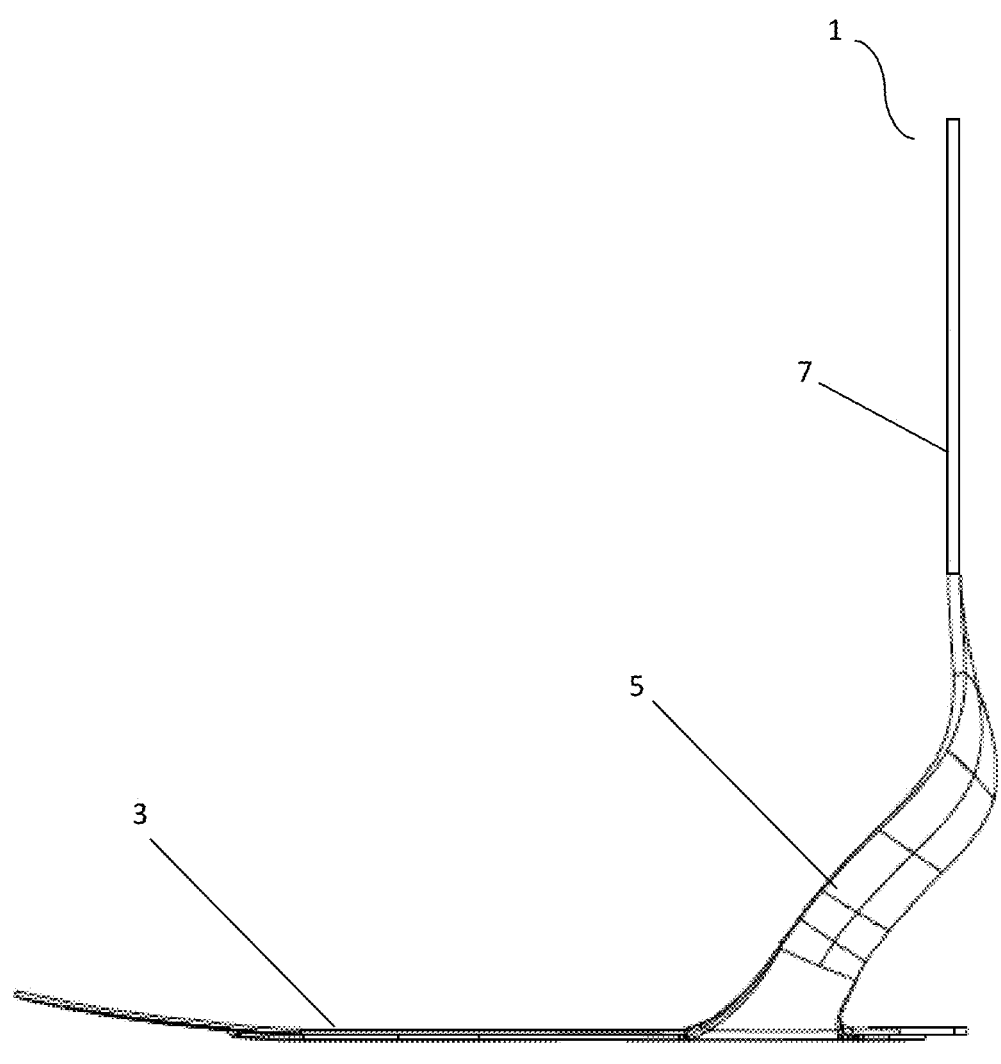
FIG. 4 is a side view of a strut portion of an exemplary embodiment of an orthosis device of the present disclosure.

The orthosis devices 100 of the present disclosure can allow for the housing member 20 to slide/move along the extension portion a pre-determined distance from a first position (FIG. 1A) to a second position (FIG. 1B). A cuff member 50 can be coupled to the hosing member 20 using any suitable means or alternatively formed as part of the housing member 20. A cuff member 50 can be formed generally in a curved shape to approximate a portion of a user's leg and can have an interior wall 51 and an exterior wall 52. In some embodiments, the strut member 1 can be manufactured out of any suitable material, including but not limited to carbon fiber, fiberglass, plastics, nylon, and/or some series of comparable materials. Similarly, the calf cuff member 50 and channel 40 could be manufactured out of carbon fiber, fiberglass, plastics, nylon, and/or some series of comparable materials. FIG. 4 illustrates a unitary embodiment of the strut member 1 having a footplate 3, curved portion 5, and extension portion 7. The extension portion 7 can extend generally in a perpendicular orientation from the footplate 3, wherein the curved portion 5 can connect the generally planar orientations of the footplate 3 and extension portion 7.

The cuff member 50 can include additional components. In some exemplary embodiments, the cuff member 50 can include a padded portion 56 that can include a band or strap portion 53. The padded portion 50 can wrap around a portion of a user's calf or leg to provide comfort and padding to a user while wearing the orthosis device 100 of the present disclosure. The strap portion can then wrap around or overlay the first side of the housing member 20 and the cuff portion 50 to secure a user's leg within the orthosis device 100. In some exemplary embodiments, the strap portion 53 can use any suitable removably coupling means, including but not limited to fasteners, hook and loop fasteners, buttons or other coupling means to secure the strap portion 53.

Figure 2A:
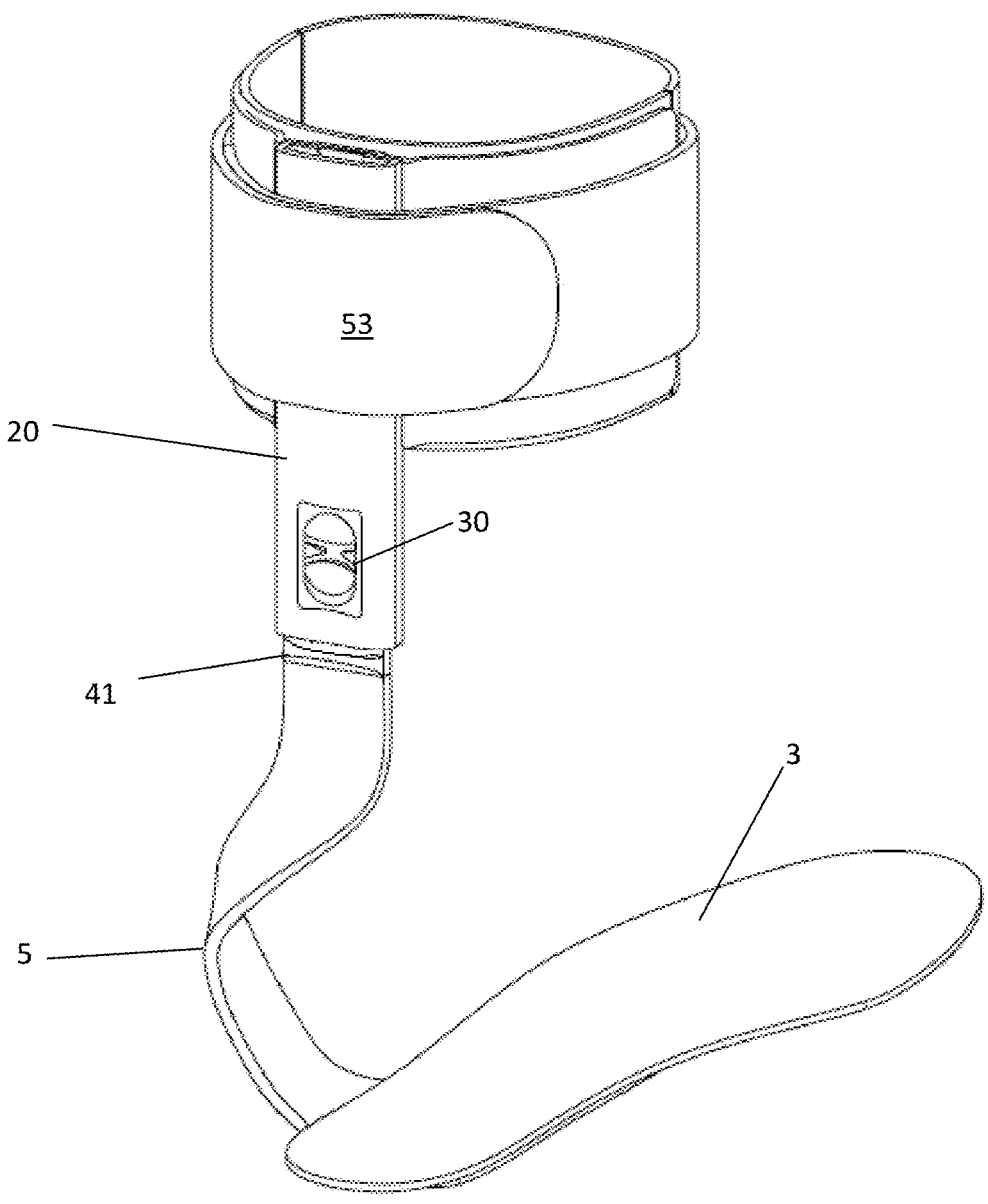
FIG. 2A is an illustration of a rear perspective view of an exemplary embodiment of an orthosis device of the present disclosure in a retracted position.
Figure 2B:
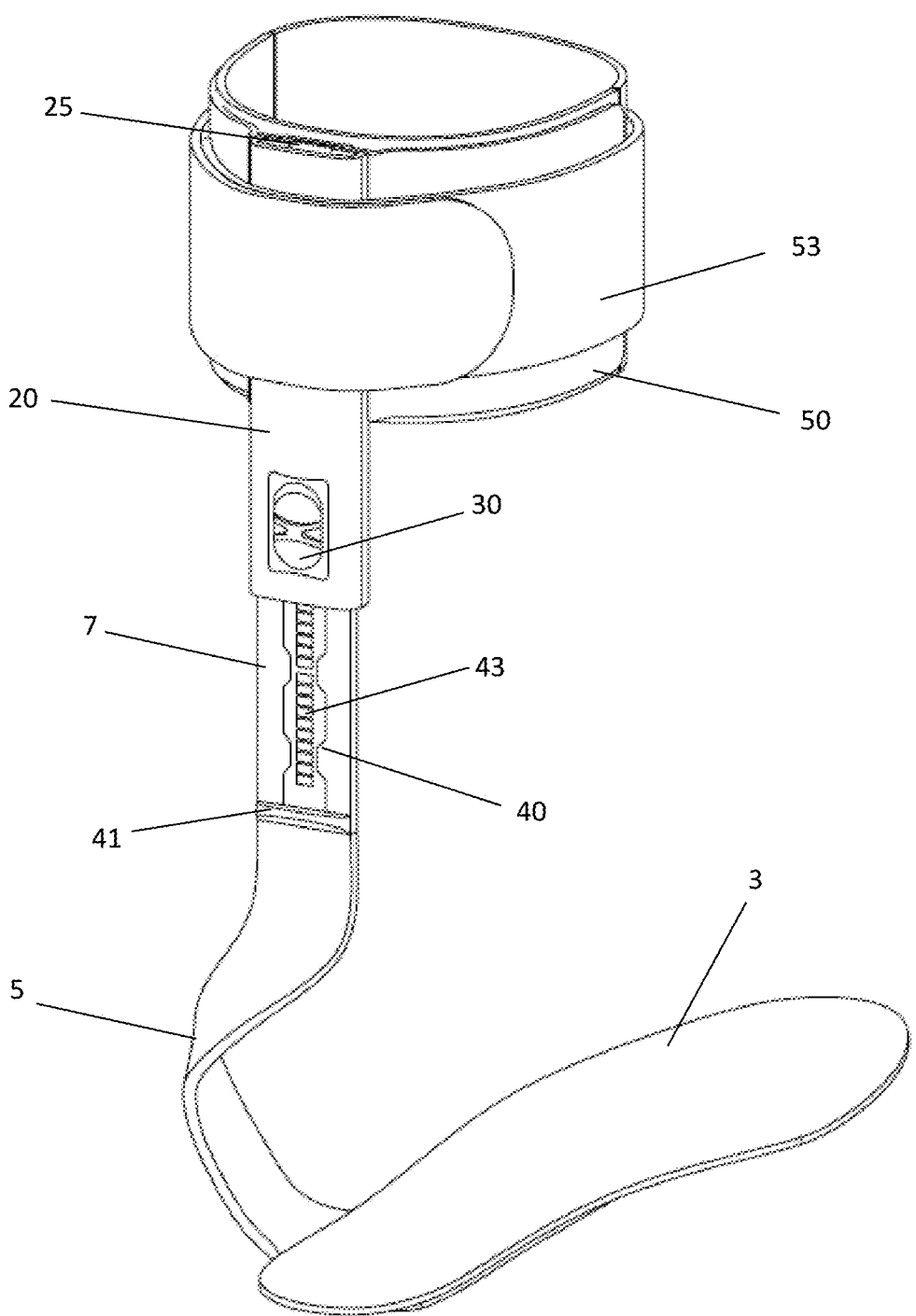
FIG. 2B is an illustration of a rear perspective view of an exemplary embodiment of an orthosis device of the present disclosure in an extended position.

As shown in FIGS. 2A-B, the locking mechanism 30 can be used to interface with a track member 40. The track member 40 can be formed on the extension portion 7 of the strut member 1 or alternatively can be removably coupled to the extension portion 7 of the strut member 1. The extension portion 7 or alternatively the track member 40 can have a stopping member/ledge 41 formed to function as a stop or rest for the housing member 20 when placed into a fully retracted position. The track member 40 can have a plurality of engagement members 43 that can interface with an interfacing member 73 of the locking mechanism 30. In some exemplary embodiments, the track portion 40 can be embedded, coupled, integrated, or otherwise designed as a portion of the strut member 1 along the extension portion 7 a pre-determined length. FIG. 2A provides an exemplary embodiment of the orthosis device 100 of the present disclosure in a first position, such as a fully retracted position. The locking mechanism can also be positioned at a first or second position. FIG. 2B illustrated an exemplary embodiment of the orthosis device 100 of the present disclosure at a second position with the locking mechanism 30 at a second position. The engagement members 43 can take any suitable configuration, including, but not limited to a formed ledge, or rung on the track that can be configured to interface with one or more interfacing members 73.

Figure 3A:
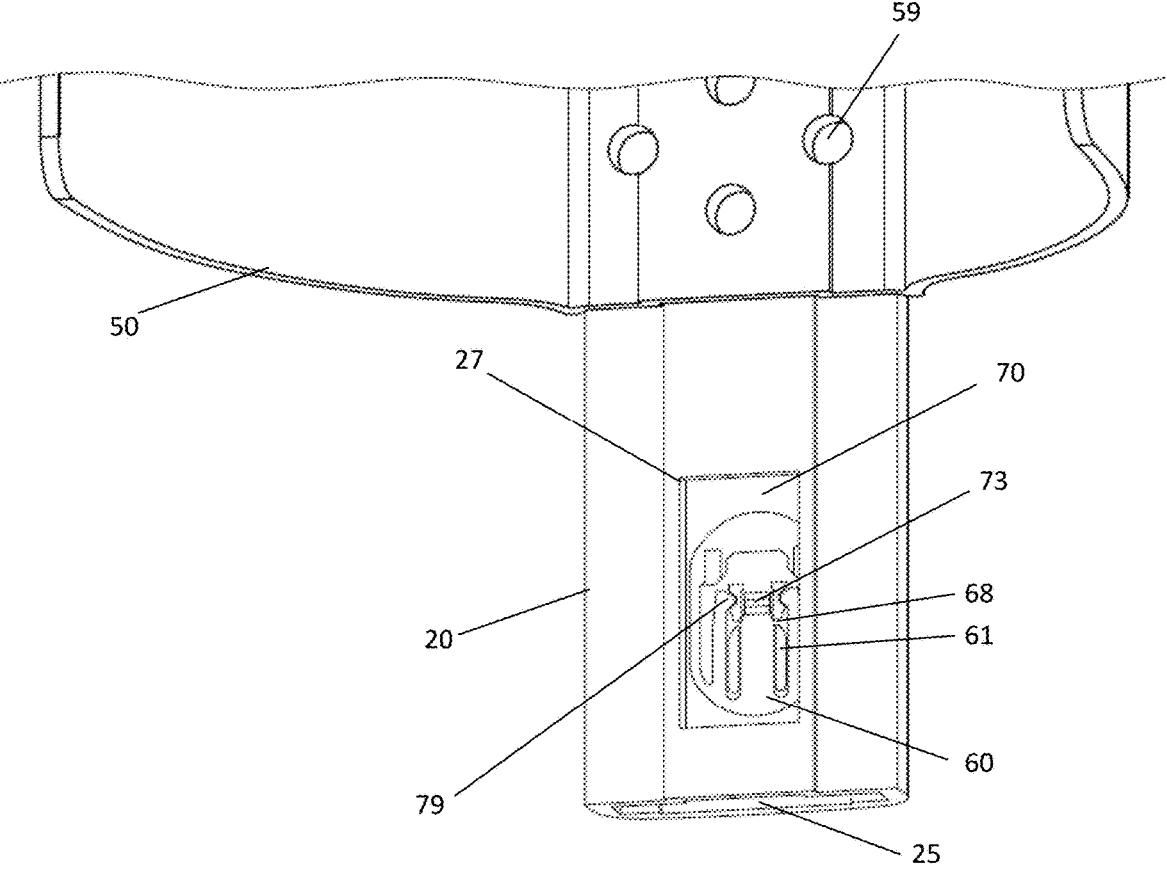
FIG. 3A is an enlarged view of a locking mechanism of an exemplary embodiment of an orthosis device of the present disclosure in a locked position.
Figure 3B:
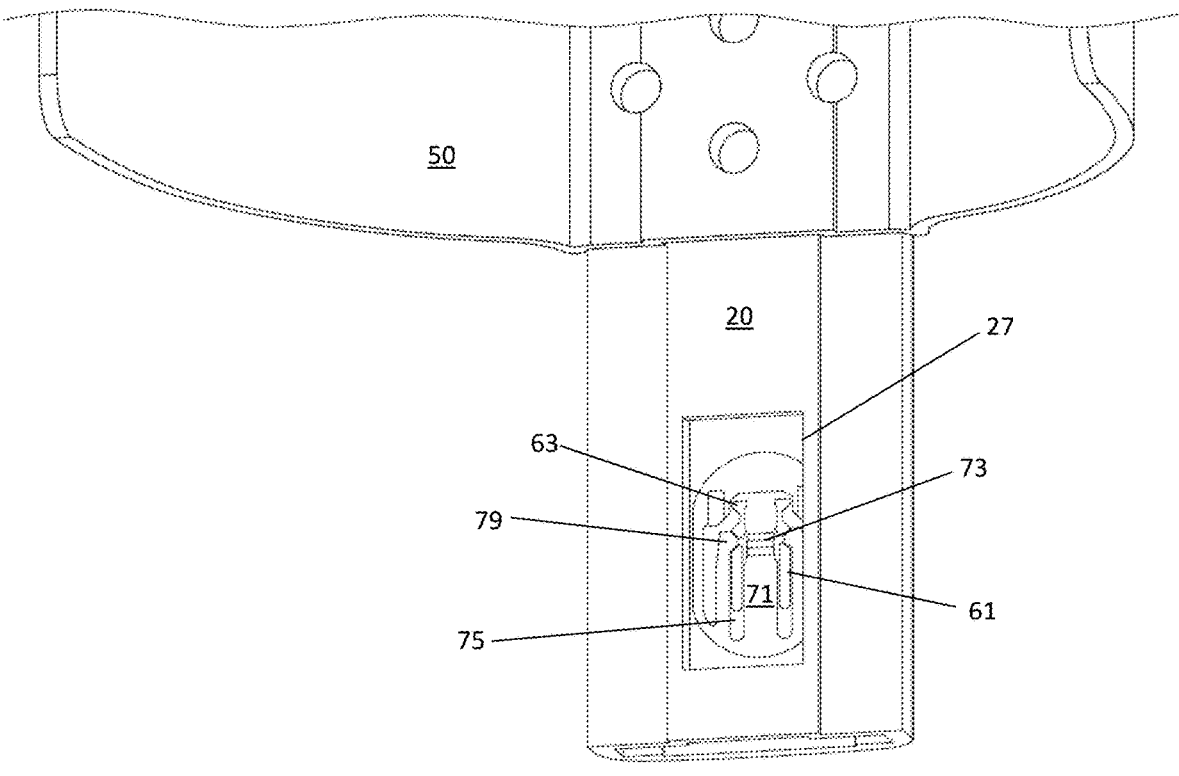
FIG. 3B is an enlarged view of a locking mechanism of an exemplary embodiment of an orthosis device of the present disclosure in an unlocked position.

FIG. 3A provides a view on the second side of the housing member with the cuff portion 50 coupled to the housing member 20. The channel 27 or opening of the housing member 20 can allow for the locking mechanism 30 to engage with the engagement members 43 of track portion 40 as the housing member 20 moves along the track portion 40. Additionally, the channel 27, can allow for a secondary locking means to be coupled a further lock the housing member 20 into place on the strut member 1. The secondary locking means can be any suitable means include a fastener to couple to an aperture 9 on the strut portion 7. In some exemplary embodiments, the primary locking means 30 can include two portions, a first portion 60 and a second portion 70. The first portion 60 can be removably coupled to the second portion 70 and can be moveable from a first position to a second position. The first and second positions can correspond to a locked/engaged and an unlocked/unengaged orientation with the engagement member 43 of the track portion 40. In some exemplary embodiments, the second portion 70 can be removably couplable with the housing member 20. FIG. 3A illustrates the locking mechanism in an engaged position without the track portion present within the housing, whereas, FIG. 3B illustrates the locking mechanism in an unlocked position.

Figure 5A:
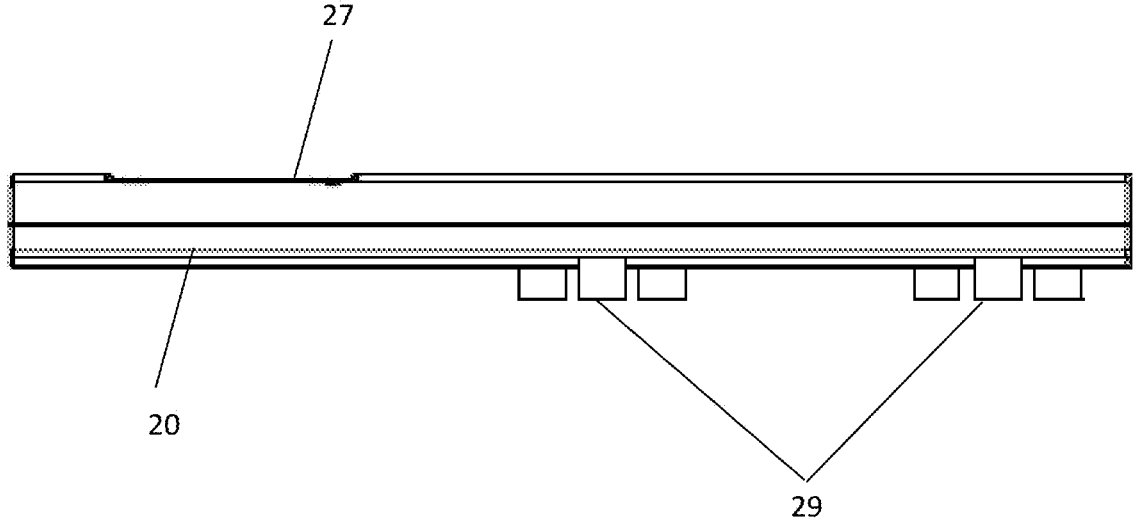
FIG. 5A is a side view of a housing member of an exemplary embodiment of an orthosis device of the present disclosure.
Figure 5B:
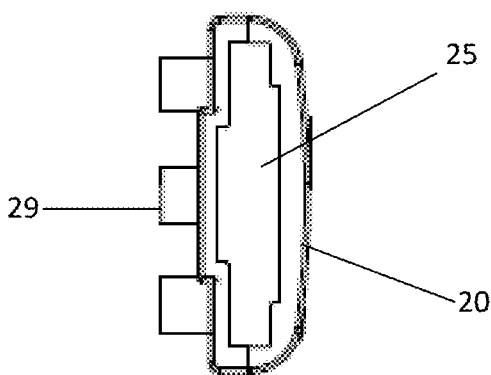
FIG. 5B is a top view of a housing member of an exemplary embodiment of an orthosis device of the present disclosure.
Figure 6:
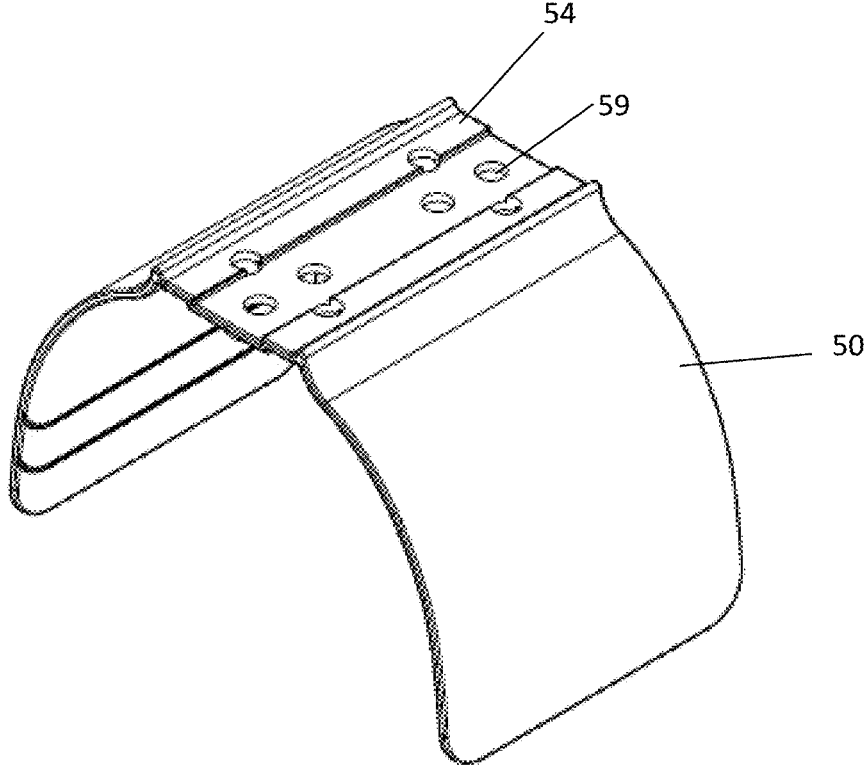
FIG. 6 is a perspective view of a cuff portion of an exemplary embodiment of an orthosis device of the present disclosure.

FIGS. 5A-B illustrated an exemplary embodiment of a housing member 20 of the present disclosure. The housing member 20 can further include one or more coupling points 29 to allow for the cuff member 50 to be removably coupled the housing member 20. The cuff member 50 can have similar coupling points 59 that can correspond to the coupling points 29 of the housing member 20, as shown in FIG. 6. The cuff member 50 can also have a recessed portion 54 to mirror the shape of the housing member 20 to allow for a better fitment between the two portions of the orthosis device 100. The housing member can additionally have a cavity 25 formed through the entire length of the housing member. The cavity 25 can take any suitable shape. In one exemplary embodiment, the shape of the cavity 25 can conform to the shape of the extension portion 7 and track portion 40 to ensure a secure fit with little movement when the extension portion 7 and the track portion are positioned within the cavity 25 of the housing member 20.

Figure 7:
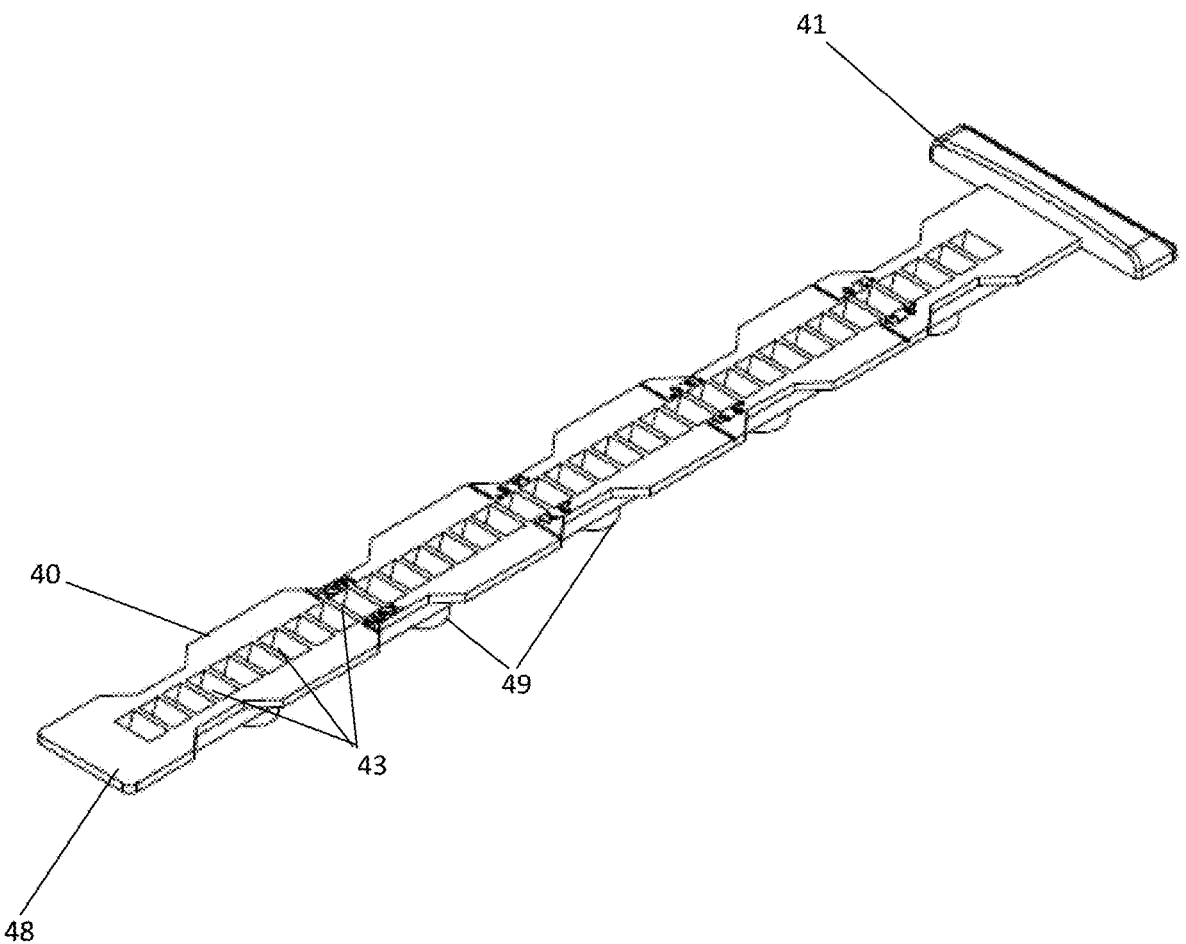
FIG. 7 is a perspective view of track portion of an exemplary embodiment of an orthosis device of the present disclosure.

As further illustrated in FIG. 7, the track portion 40 can have a plurality of engagement members 43. The engagement members 43 can take any suitable shape, including but not limited to rungs, teeth, or steps that allows for a corresponding locking mechanism to engage the and lock the housing member 20 in a first position along the track portion 40. The locking mechanism 30 and track 40 allow for the housing member 20 to be adjusted up and down some length of the track portion 40, and secured to the track system and strut in several different heights that correspond with the engagement member 43 of the track portion 40. This enables a user to easily adjust the height of the housing member 20 and corresponding cuff portion 50 to best fit a user and similarly allow for a universal orthosis without the need to have special orthosis devices made from scratch to accommodate user's varying heights. In some embodiments, the track portion 40 can be manufactured out of carbon fiber, fiberglass, plastics, nylon, and/or some series of comparable materials. In some embodiments, the track portion can further include an upper and/or lower stopping mechanism 41 that would prevent the cuff from sliding below or above certain heights. On or more coupling points 49 can be formed a second surface of the track portion 40. The coupling points 49 can correspond to the apertures 9 on the extension portion 7 to provide a means to couple the track portion 40 to the extension portion 7 in certain exemplary embodiments.

Figure 8A:
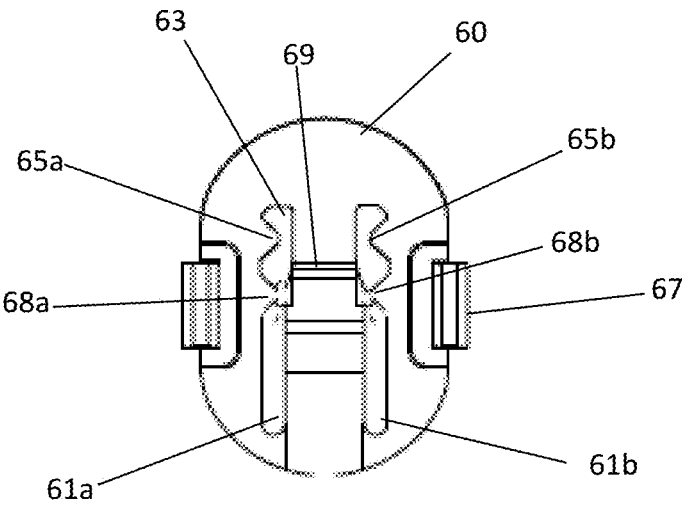
FIG. 8A is a front view of a slider portion of a locking mechanism of an exemplary embodiment of an orthosis device of the present disclosure.
Figure 8B:
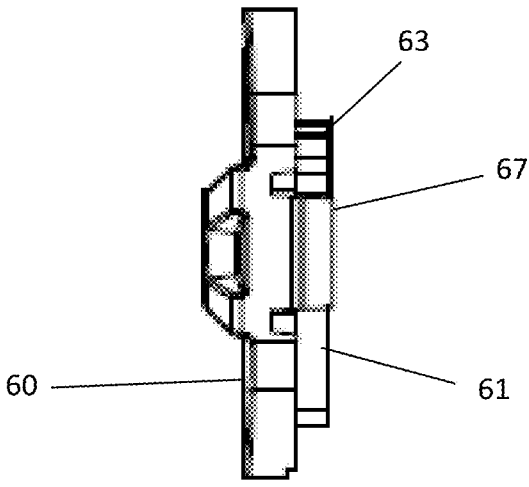
FIG. 8B is a side view of a slider portion of a locking mechanism of an exemplary embodiment of an orthosis device of the present disclosure.

FIGS. 8A-8B illustrate an exemplary embodiment of a first portion 60 of a locking mechanism of an orthosis device of the present disclosure. The first portion 60 can include one or more guide member 61 and one or more locking guides 63 that can have recessed portion 65 that can interface with a locking member 79 of the other portion 70. A groove 68 or recess can be formed between the locking guides 63 and the guide member 61. The grooves 68*a,b* can interface with one or more corresponding locking members 79 to engage the locking mechanism in a first position. The recessed portions 65*a,b* can allow for the first portion to be locked in to a second position. Additionally, it can cause the engagement of an interfacing member 73 with an engagement member 43 of the track portion 40. One or more coupling members 67 can be included to couple the first portion 60 to the second portion 70 of the locking mechanism. The first portion can also have a raised area 69 positioned between the locking guides 63.

Figure 9A:
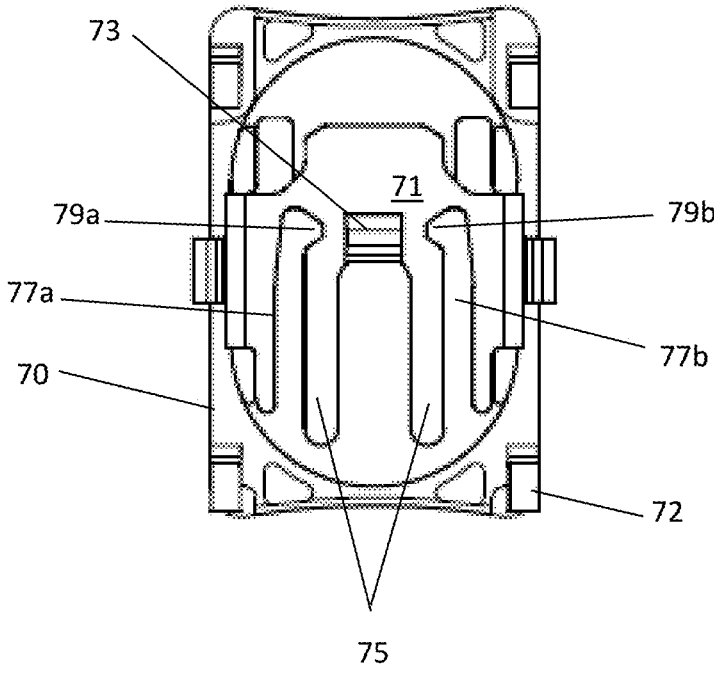
FIG. 9A is a front view of a locking portion of a locking mechanism of an exemplary embodiment of an orthosis device of the present disclosure.
Figure 9B:
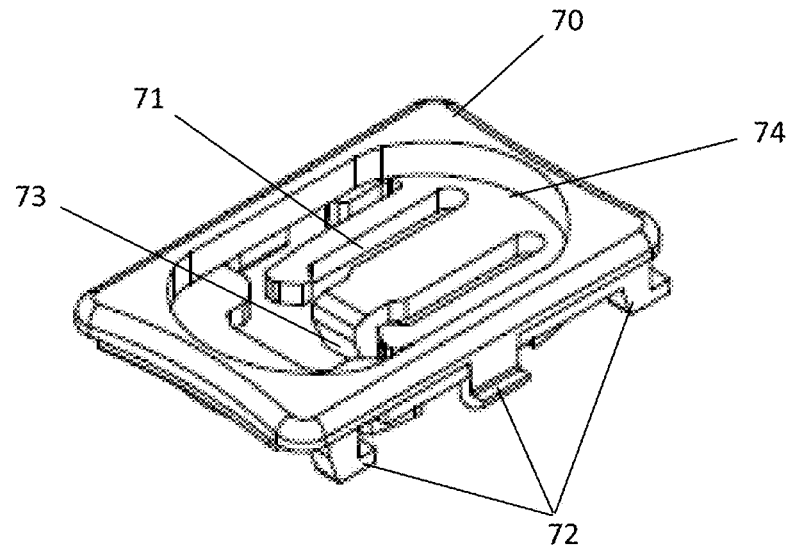
FIG. 9B is a perspective view of a locking portion of a locking mechanism of an exemplary embodiment of an orthosis device of the present disclosure.

As shown in FIGS. 9A-B, the second portion 70 of the locking mechanism 30 can include a central member 71 that can extend generally down from a first top edge of the second portion 70 a pre-determined distance. At the end of the central member can be a raised portion or interfacing member 73 that can engage the engagement member 30 of the track portion 40 when the locking mechanism is the locked position. Each side of the central member 71 can be one or more channels 75. The interfacing member 73 can have a hook or ledge that extends out from the central member pre-determined distance. The corresponding guide members 61 of the first portion can move slide within the channels 75 from a first position to a second position. Additionally, one or more locking arms 77 can extend from a first edge of the second portion.

When the first portion 60 of the locking mechanism 30 is moved into the locked position, the one or more locking members 79 can engage the one or more recessed portions 65. The raised area 69 can then engage or contact the central member 71 and case the central member to extend the interfacing member 73 from a first plane to a second plane to allow for the interfacing member 73 to engage the engagement member 43. The second portion 70 can additionally have one or more coupling members 72 to interface with the housing member 20 and couple the locking mechanism to the housing member 20. The coupling members 72 can take any suitable form such as a hook or ledge to allow a compression coupling between the housing member 20 and the second portion 70 to allow for a removably couplable component. The second portion can additionally have an inset area 74 to provide space for the first portion 60 to be partially or optionally fully housed within the inset area 74 of the second portion 70. The first portion 60 can be slidable between a first position and a second position within the inset area 74.

As illustrated in FIGS. 2A-B and 3A-B, a first portion 60 of the locking mechanism can be slidable from a first position to a second position within the second portion 70 of the locking mechanism 30. The channels 75 and guide members 61 can help maintain the movement of the first portion along a plane between the two positions. In some exemplary embodiment, the first position can be an unlocked position and the second position can be a locked position. When the locking mechanism 30 is in the locked position, the interfacing member can engage one of the engagement members 43 to lock the housing portion in position at that particular engagement member 43 position on the track portion 40.

An exemplary embodiment of the orthosis device 100 of the present disclosure can utilize various components and different locking mechanisms as shown in FIGS. 10-12. The apparatus can similarly include a strut member 1, a housing member 20, a locking mechanism 30, a track portion 40, and a cuff portion 50. The various components of the apparatus can be removably coupled to one another through one or more fasteners. The locking mechanism 30 can be removably coupled to the housing member 20 and engage the track portion 40 of the application to lock the housing member 20 at a position along the track portion 40. FIGS. 10A-B provide an exemplary embodiment of the apparatus of the present disclosure utilizing a locking mechanism 30 that interfaces with the housing 20 and the track 40 of the apparatus 100.

Figure 10A:
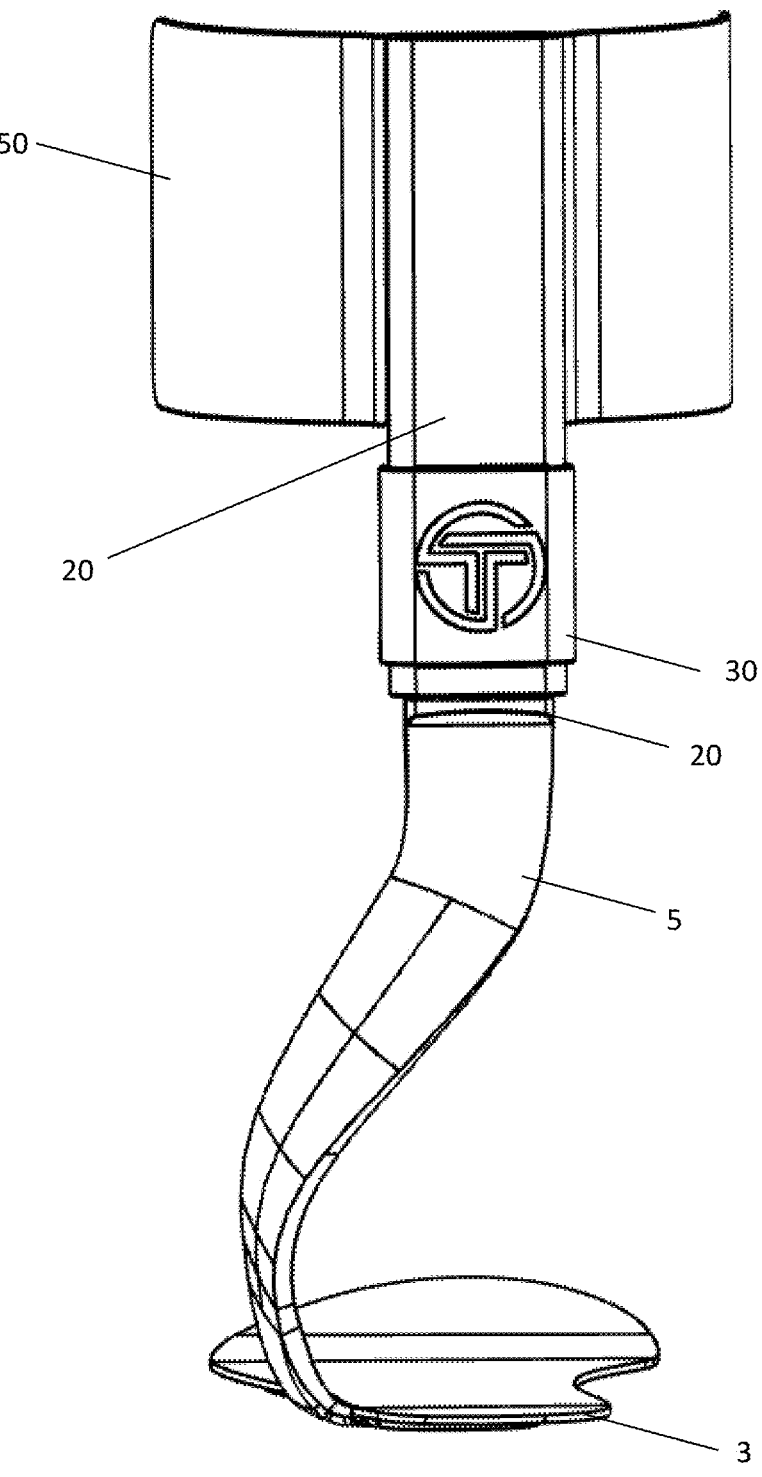
FIG. 10A is an illustration of a rear view of an exemplary embodiment of an orthosis device of the present disclosure.
Figure 10B:
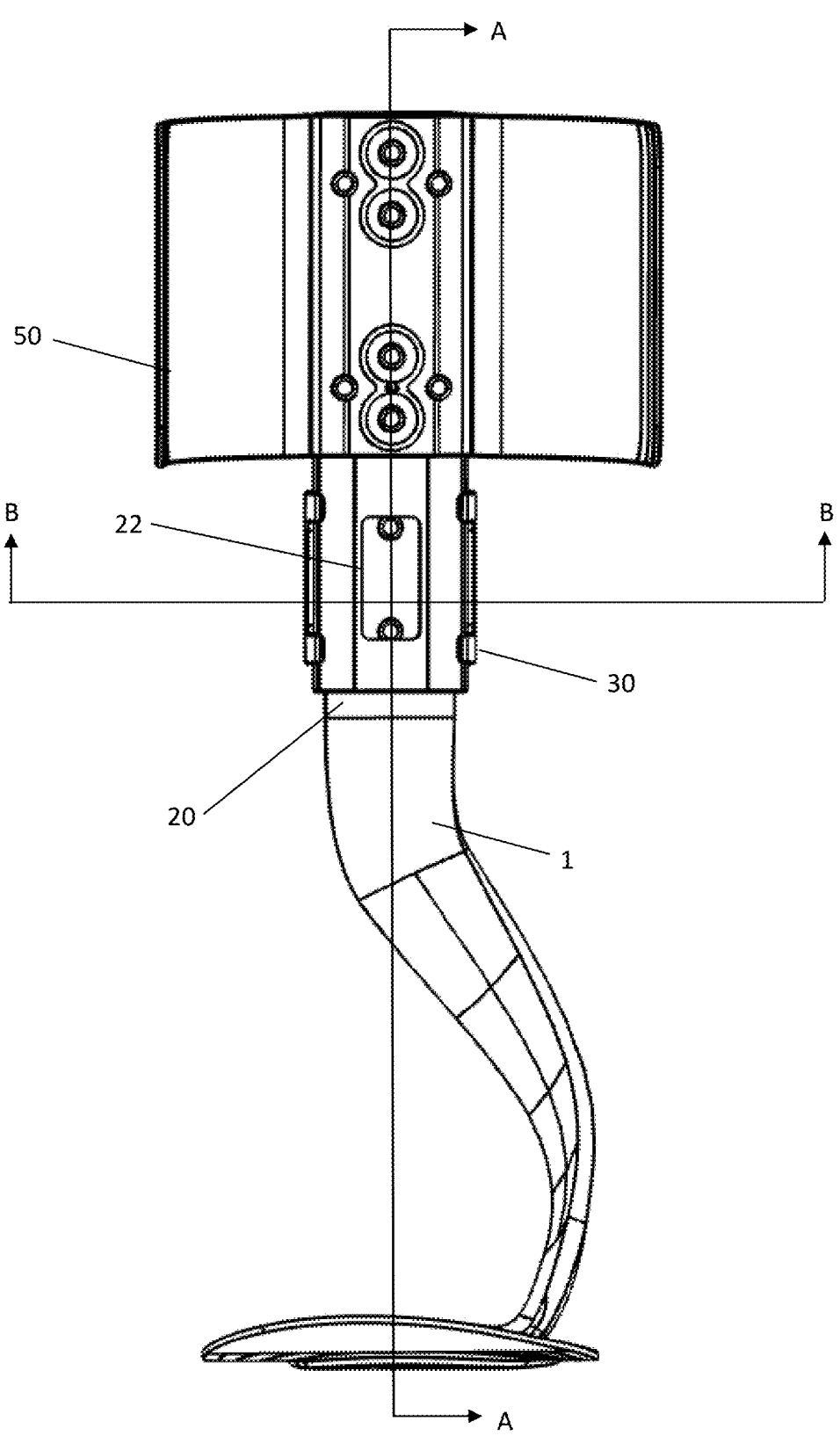
FIG. 10B is an illustration of a front view of an exemplary embodiment of an orthosis device of the present disclosure.
Figure 10C:
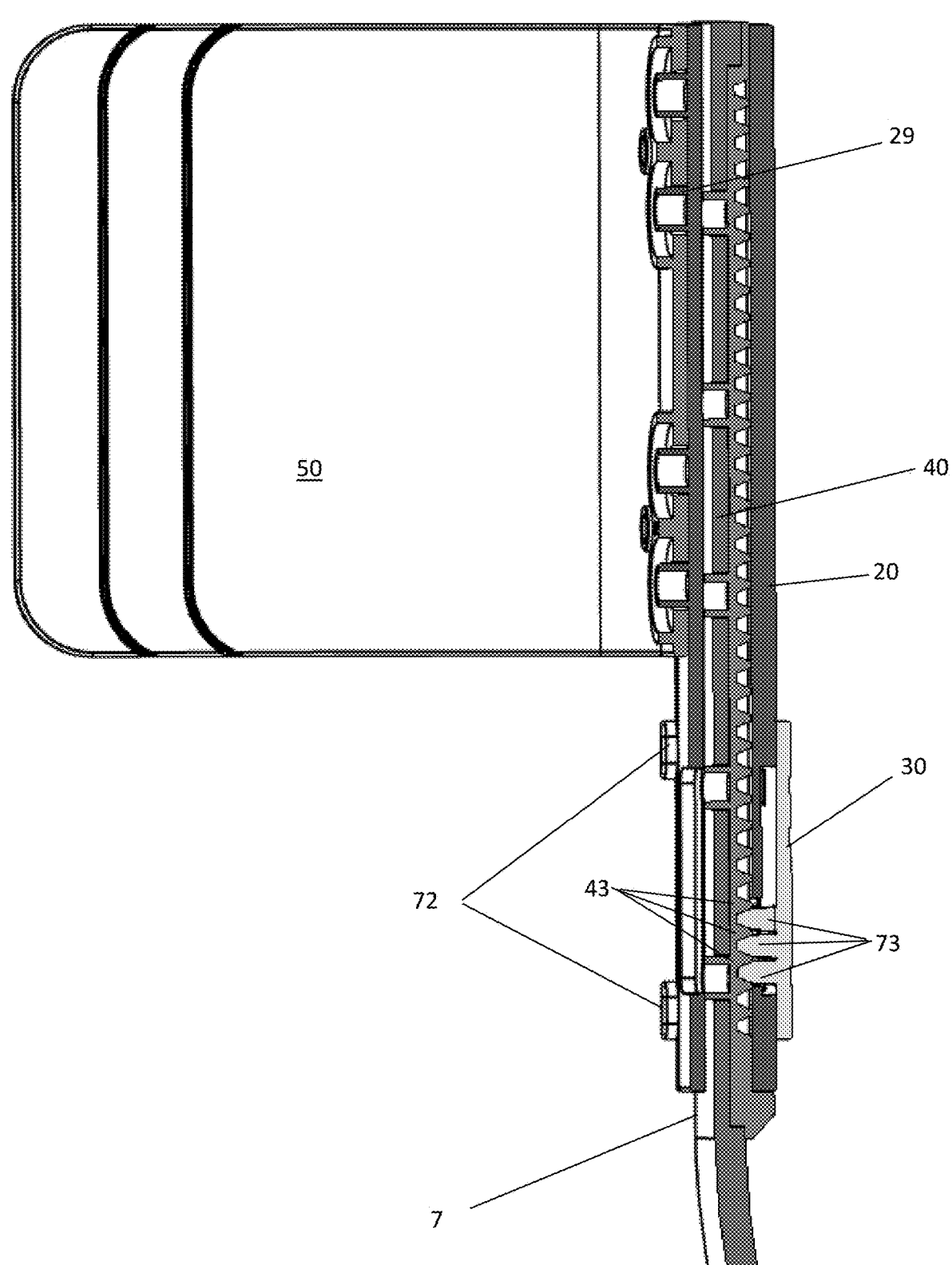
FIG. 10C is an illustration of an enlarged cross-section side view of an exemplary embodiment of an orthosis device of the present disclosure along axis A-A of FIG. 10B.
Figure 10D:
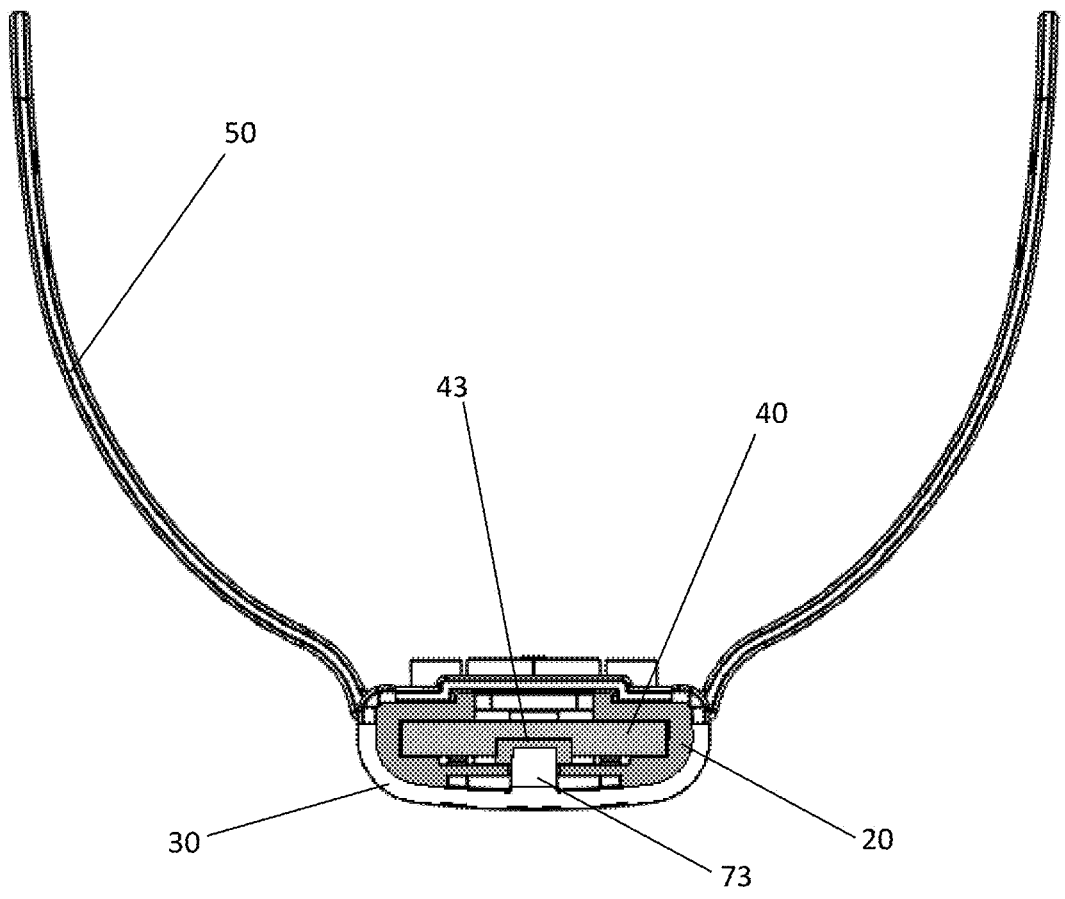
FIG. 10D is an illustration of an enlarged cross-section bottom view of an exemplary embodiment of an orthosis device of the present disclosure along axis B-B of FIG. 10B.
Figure 10E:
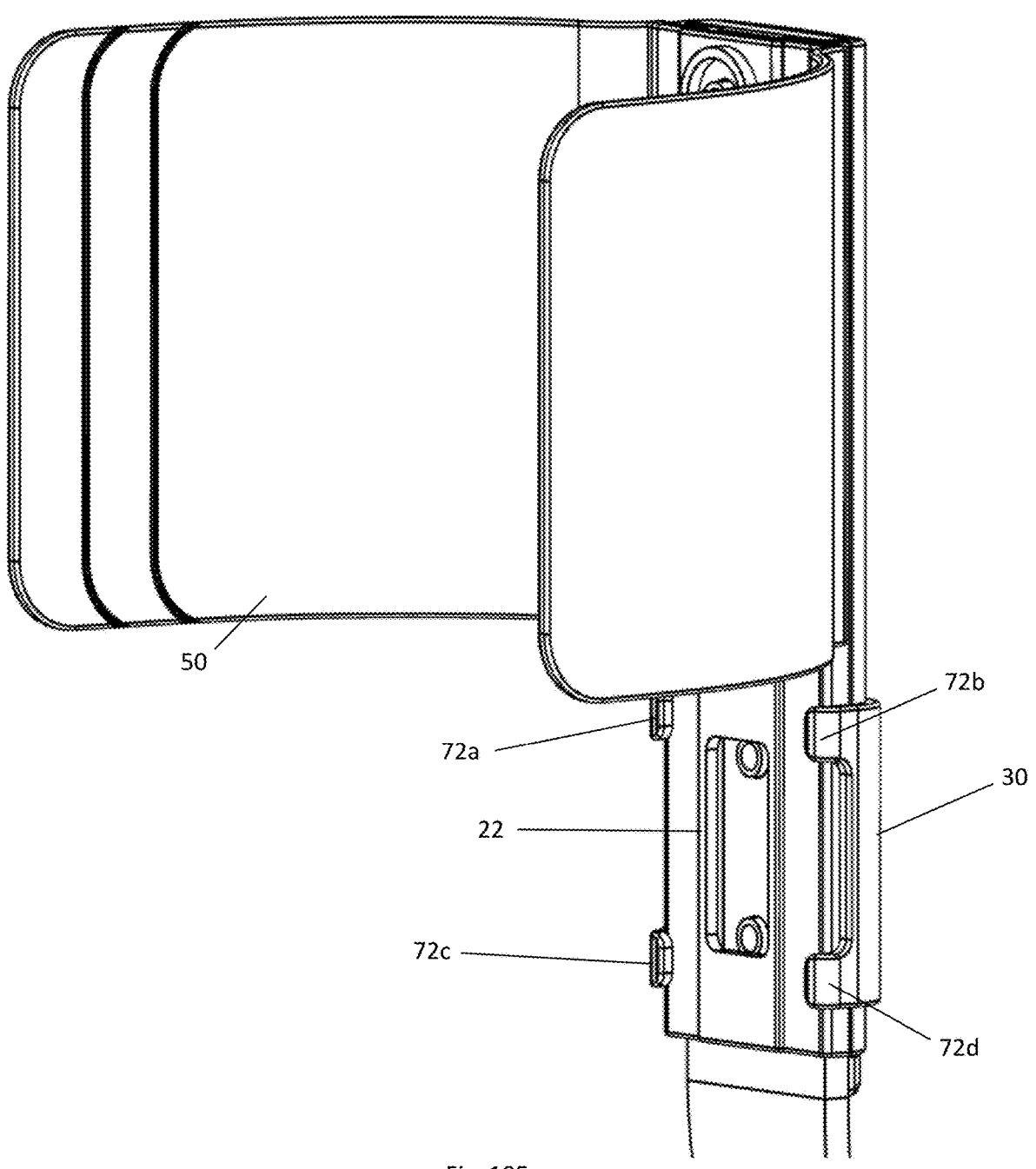
FIG. 10E is an illustration of an enlarged perspective view of an exemplary embodiment of an orthosis device of the present disclosure.

As shown in FIGS. 10C-D, one or more engagement members 43 that can interface with one or more interfacing members 73 of the locking mechanism 30. In some exemplary embodiments, the track portion 40 can be embedded, coupled, integrated, or otherwise designed as a portion of the strut member 1 along the extension portion 7 a pre-determined length. The locking mechanism 30 can also be positioned at a first or second position relative to the track portion 40. The locking mechanism 30 can be removably coupled to the housing member 20 to lock the housing member 20 into one or more positions as it is moved up or down the track portion 40 of the device 100. The engagement members 43 can take any suitable configuration, including, but not limited to a formed ledge, or rung on the track 40 that can be configured to interface with one or more interfacing members 73.

Figure 11A:
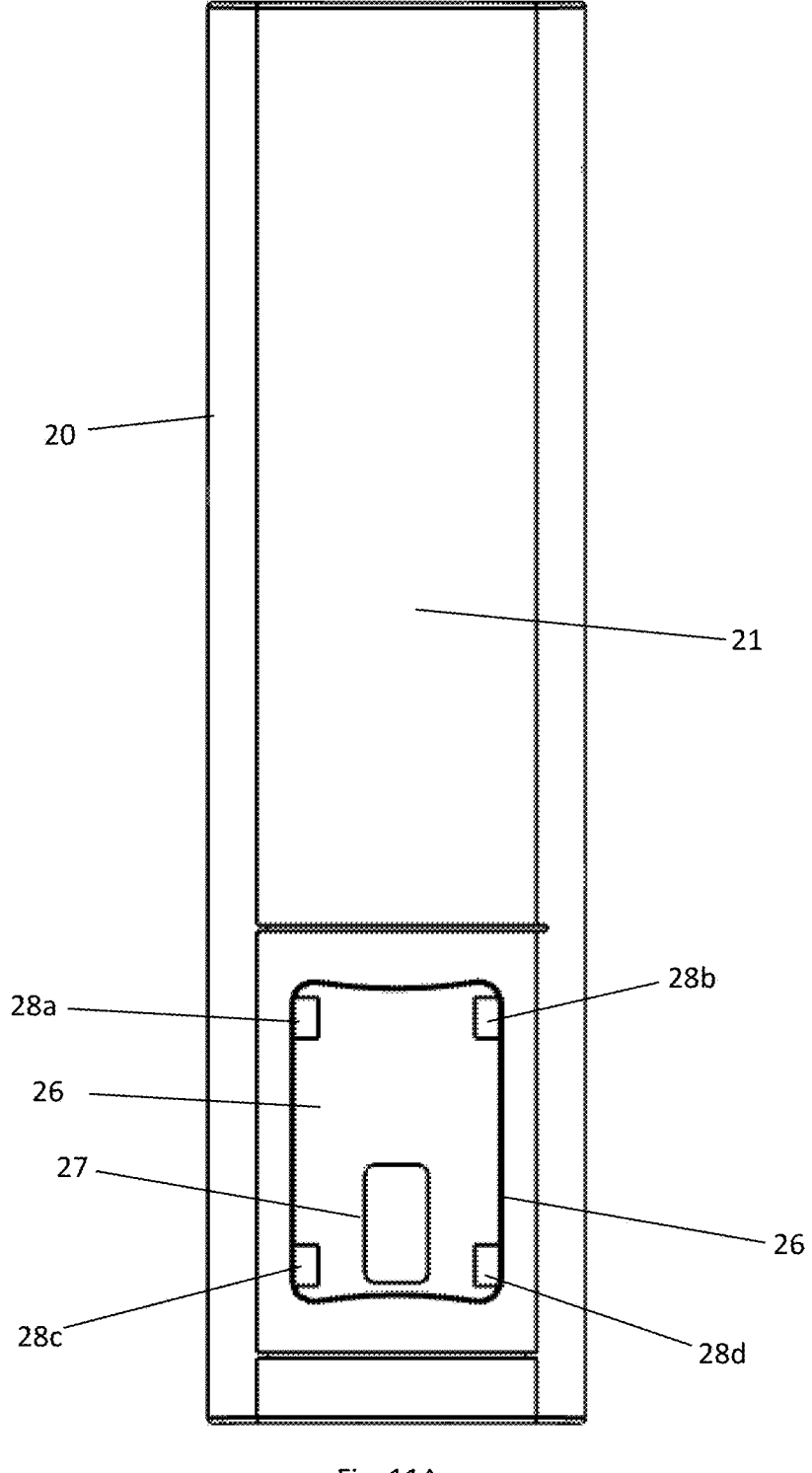
FIG. 11A is a rear view of a housing member of an exemplary embodiment of an orthosis device of the present disclosure.
Figure 11B:
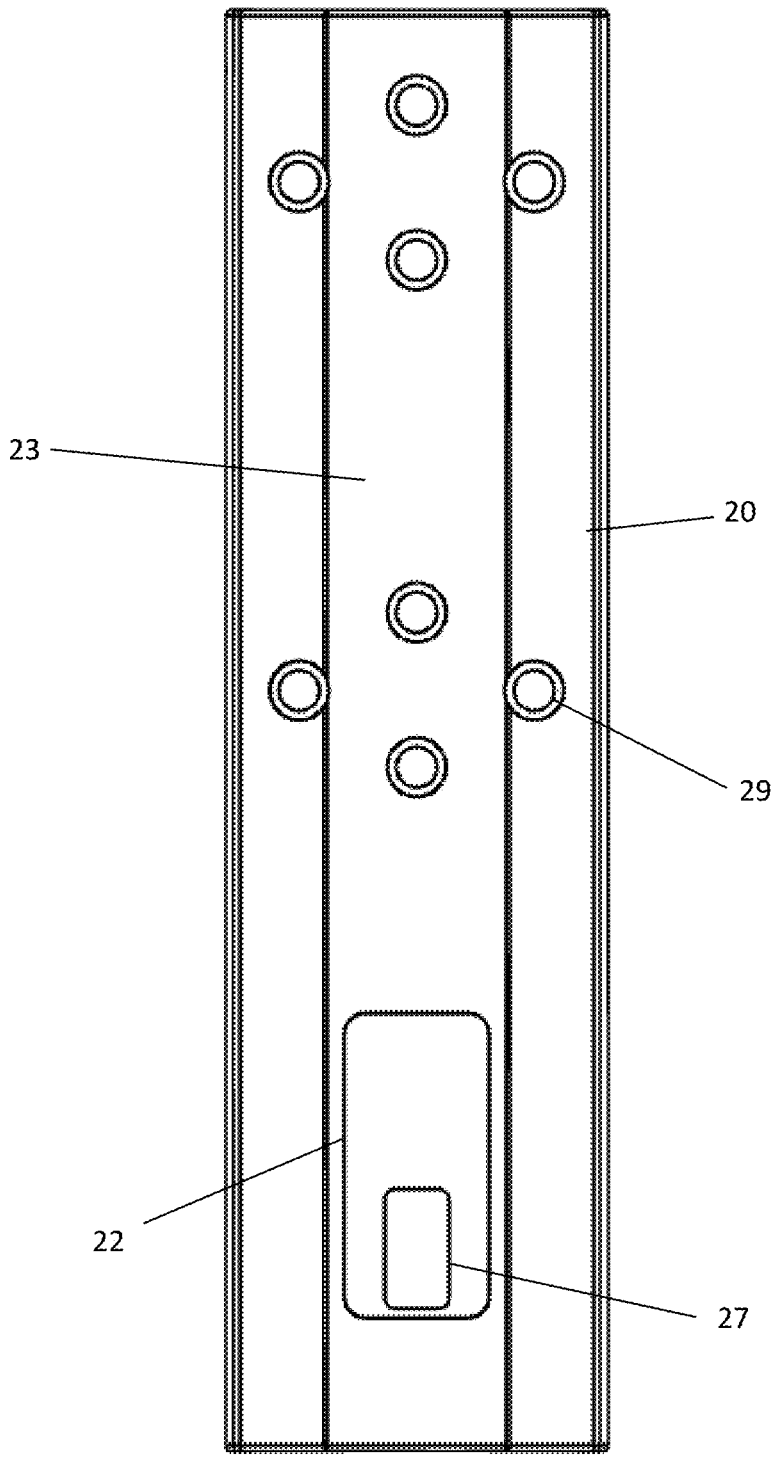
FIG. 11B is a front view of a housing member of an exemplary embodiment of an orthosis device of the present disclosure.
Figure 11C:
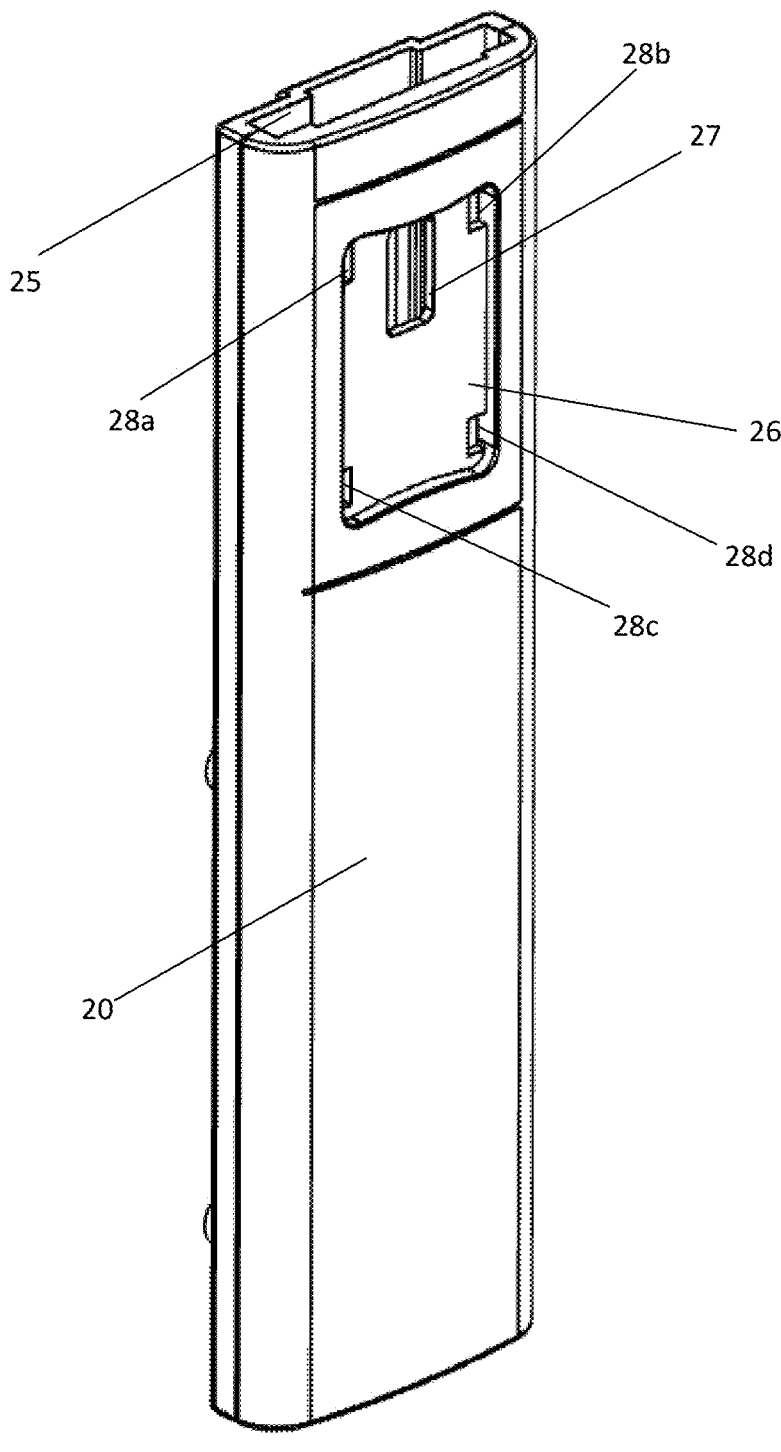
FIG. 11C is a perspective view of a housing member of an exemplary embodiment of an orthosis device of the present disclosure.

FIGS. 11A-C illustrate an exemplary embodiment of a housing member 20 of the orthosis device 100 of the present disclosure. The housing member 20 can have a first surface 21 and a second surface 23. The first surface 21 can be generally on the exterior side of the orthosis device 100. The housing member 20 can have a first opening 27 on the first side 21 that provides access into the interior of the housing member and the track portion 40 positioned within the housing member 20. The housing member 20 can optionally have a second opening 22 on the second side 23. In some exemplary embodiments, the housing 20 can have an optional recessed portion 26 with a surface at plane at a different pane that the top surface 21 of the housing member 20.

In some exemplary embodiments, the housing member 20 can additionally have one or more locating apertures 28 configured to interface with one or more corresponding optional locating members 78 of the locking mechanism 30. The locating members 78 can help position the locking mechanism 30 when coupling the locking mechanism 20 to the housing member 20. The locating members 78 can extend a pre-determined distance from the surface of the second side 33 of the locking portion 30 as shown in FIG. 12C.

In some exemplary embodiments, the locating member(s) 78 can also function as additional coupling members to further couple the locking mechanism 30 to the housing 20. In one exemplary embodiment, the housing member 20 can have a plurality of locating apertures 28a,b,c,d and the locking member 30 can have corresponding locating members 78a,b,c,d. The locking member 30 can generally use a compression fit without needing any additional coupling components. In some exemplary embodiments, a secondary coupling means such as a fastener to provide a secondary coupling means to further prevent the locking member 30 from coming uncoupled from the housing member 20. In other exemplary embodiments, the locating members 78 and corresponding apertures 28 can be optional.

The housing member 20 can further include on or more coupling points 29 or apertures to allow for the cuff member 50 to be removably coupled the housing member 20. The cuff member 50 can have similar coupling points 59 that can correspond to the coupling points 29 of the housing member 20, as shown in FIG. 10C. The cuff member 50 can also have a recessed portion 54 to mirror the shape of the housing member 20 to allow for a better fitment between the two portions of the orthosis device 100. The housing member 20 can additionally have a cavity 25 formed through the entire length of the housing member. The cavity 25 can take any suitable shape. In one exemplary embodiment, the shape of the cavity 25 can conform to the shape of the extension portion 7 and track portion 40 to ensure a secure fit with little movement when the extension portion 7 and the track portion are positioned within the cavity 25 of the housing member 20.

Figure 12A:
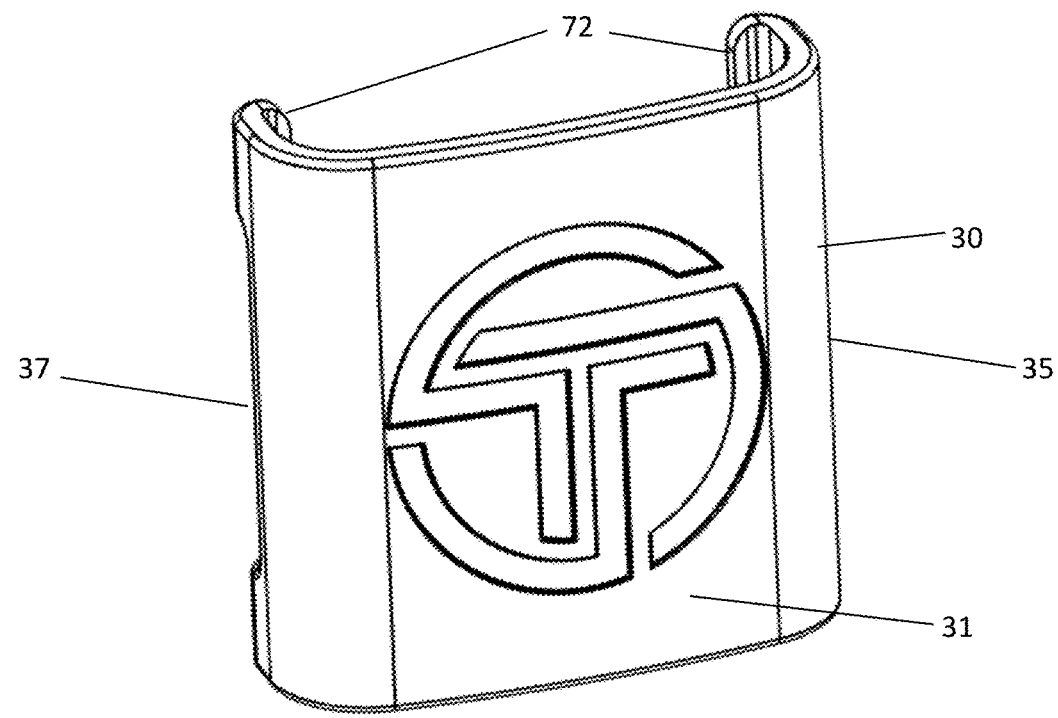
FIG. 12A is a rear perspective view of a locking mechanism of an exemplary embodiment of an orthosis device of the present disclosure.
Figure 12B:
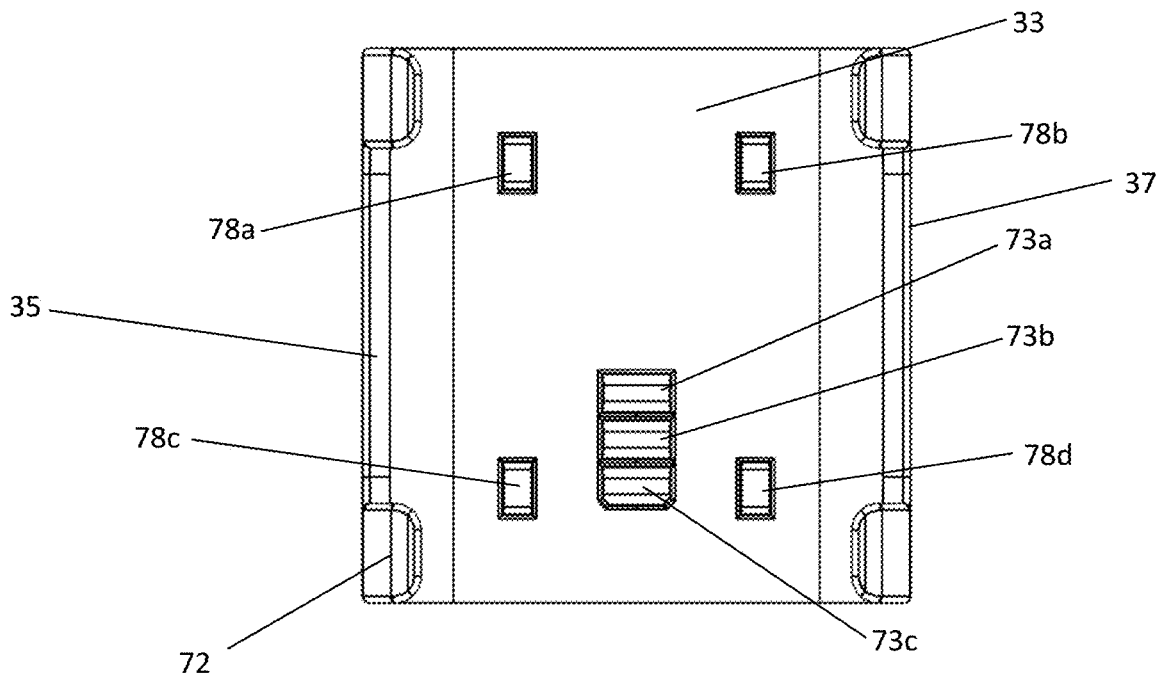
FIG. 12B is a front perspective view of a locking mechanism of an exemplary embodiment of an orthosis device of the present disclosure.
Figure 12C:
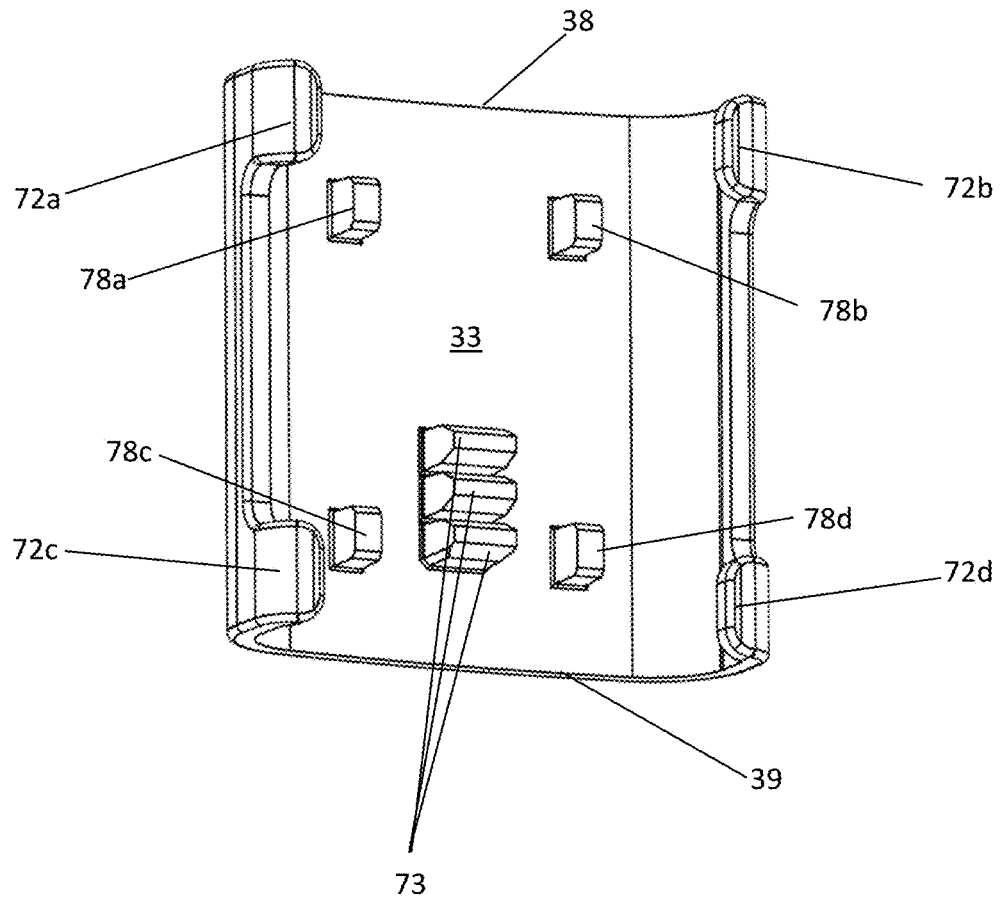
FIG. 12C is a front view of a locking mechanism of an exemplary embodiment of an orthosis device of the present disclosure.

As shown in FIG. 12A-C, an exemplary embodiment of a locking mechanism 30 of the present disclosure can have a first side 31 and a second side 33. One or more coupling members 72 can be formed on a second side 33 of the locking member 30. The coupling members 72 can extend from the first surface of the locking mechanism 30 to form a curved portion that can approximate and extend around the edge of the housing member 20 as shown in FIGS. 10A-F. The locking member 30 can have four side edges to generally define the shape of the locking member 30. In some exemplary embodiments, the top side edge 38 and bottom edge 39 can be generally planar. The other side edges can be formed to approximate a sidewall of a housing member 20. The first side edge 35 and second side edge 37 can have one or more curved portions that can further extend from the respective side edges to form the coupling member(s) 72a,b,c,d as shown in FIG. 12C. In other exemplary embodiments, the entire first side edge 35 and second side edge 37 can form a coupling member 72 or curved portion to wrap around the edge of the housing member 20 and interface with the second side 23 of the housing member 20. The top edge 38 and bottom edge 39 can define the length of the locking member 30.

Figure 10F:
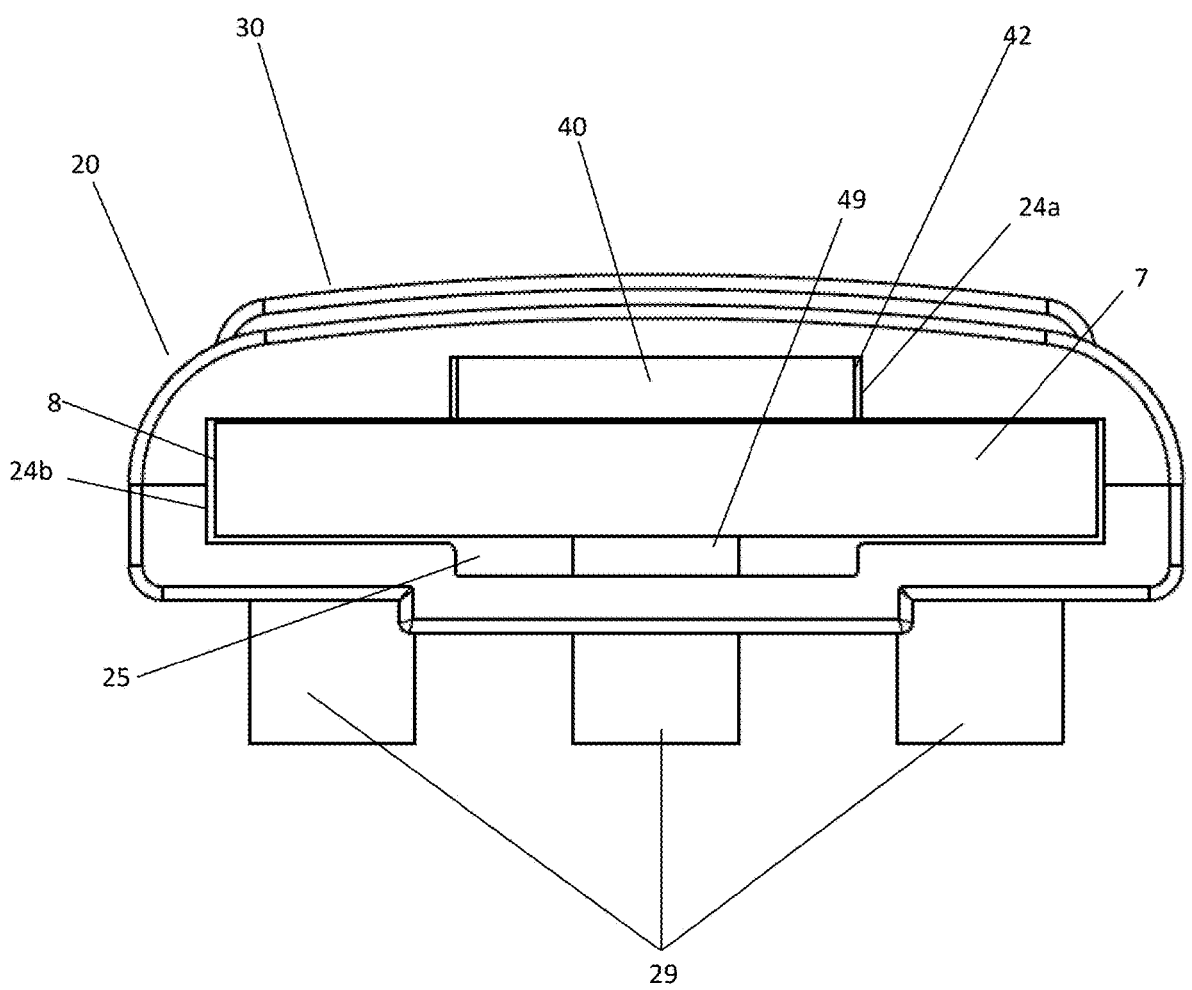
FIG. 10F is an illustration of a top view of an exemplary embodiment of an orthosis device of the present disclosure without the cuff portion.

FIG. 10F illustrates a top view of an exemplary embodiment of the apparatus without the cuff portion 50 having a housing member 20 and locking member 30. The extension portion 7 can have a track portion 40 removably coupled, affixed, or formed to the extension portion 7. The track portion 40 can have a sidewall 42. The cavity 25 formed through the entire length of the housing member 20 can conform to the shape of the extension portion 7 and track portion 40 to ensure a secure fit with little movement when the extension portion 7 and the track portion are positioned within the cavity 25 of the housing member 20. The sidewall 42 of the track portion 40 can slidably interface with a sidewall portion 24a of the housing or alternatively have minimal spacing from the sidewall portion to ensure little to not radial or lateral movement of the housing member on the extension portion 7. Similarly, a second sidewall portion 24b can slidably interface with a sidewall 8 of the extension portion or alternatively be minimally spaced from the sidewall 8 to further prevent lateral and radial movement of the extension portion 7 within the housing cavity.

In some exemplary embodiments, the track portion 40 can be removably coupled to the extension portion 7. Alternatively, the track portion 40 can be formed as part of the extension 7. The track portion 40 can extend upward from the surface of a first side of the strut portion a predetermined distance to from a sidewall 42. A surface of the track portion can have a plurality of engagement member 43 for interfacing with the locking mechanism to allow for the adjustability of the housing members 20 position along a length of the extension portion.

The locking mechanism 30 can have one or more interfacing members 73. In one exemplary embodiment, the locking member 30 can have a plurality of interfacing members 73a,b,c that can interface with the engagement members 43 of the track portion 40 as shown in FIG. 10C. The locking mechanism 30 can be removably coupled to the housing member to allow for the housing member 20 to be slid or moved between a plurality positions of the track portion 40. This can allow a user to adjust the height of the cuff member to a user desired position. The locking member 30 can then be positioned back onto the housing member 20 to interface with the housing member 20 and track 40 to lock the housing member 20 into position a desired position to prevent movement of the housing member 20.

Figure 13:
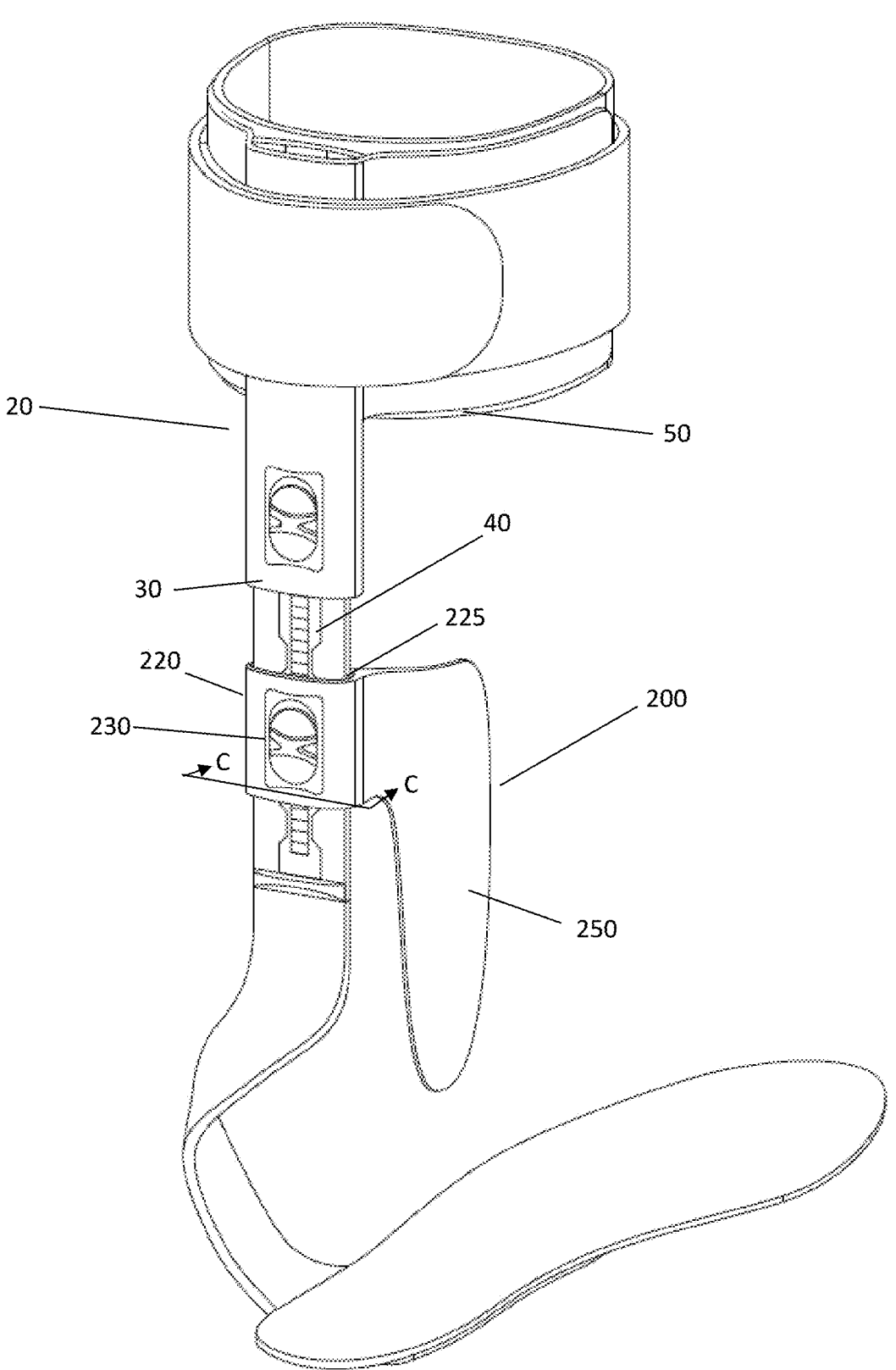
FIG. 13 is a rear perspective view of an exemplary embodiment of an orthosis device of the present disclosure having a secondary attachment component.

The apparatus of the present disclosure can further include a secondary attachment component 200 or secondary support member that can be removably coupled to the track portion 40 as shown in FIG. 13. In some exemplary embodiments, the secondary attachment 200 or support component can utilize and include the same or similar locking or coupling mechanism 230 as the locking mechanism 30 for the housing member 20 shown in FIGS. 1-3 and FIGS. 10A-F respectfully. The housing portion 220 and locking mechanism 230 can be used to couple and lock into place the housing at a position along the track 40 and a locking mechanism 230 can be provided to lock the secondary attachment component 200 at a desired position on the track 40. The secondary attachment 200 can take any suitable configuration. The secondary attachment component 200 can have a housing portion 220 that can have an opening 225 therethrough similar to the housing portion shown in FIG. 10F. The opening can approximate shape of the track portion similar to the housing 20. A flange 250 or support portion can extend from an edge of the housing portion 220. In some exemplary embodiments, the flange can be configured as a varus or valgus flange 250 that can provide inversion or eversion control depending upon the side of the leg it is configured to interface with a user.

Figure 14:
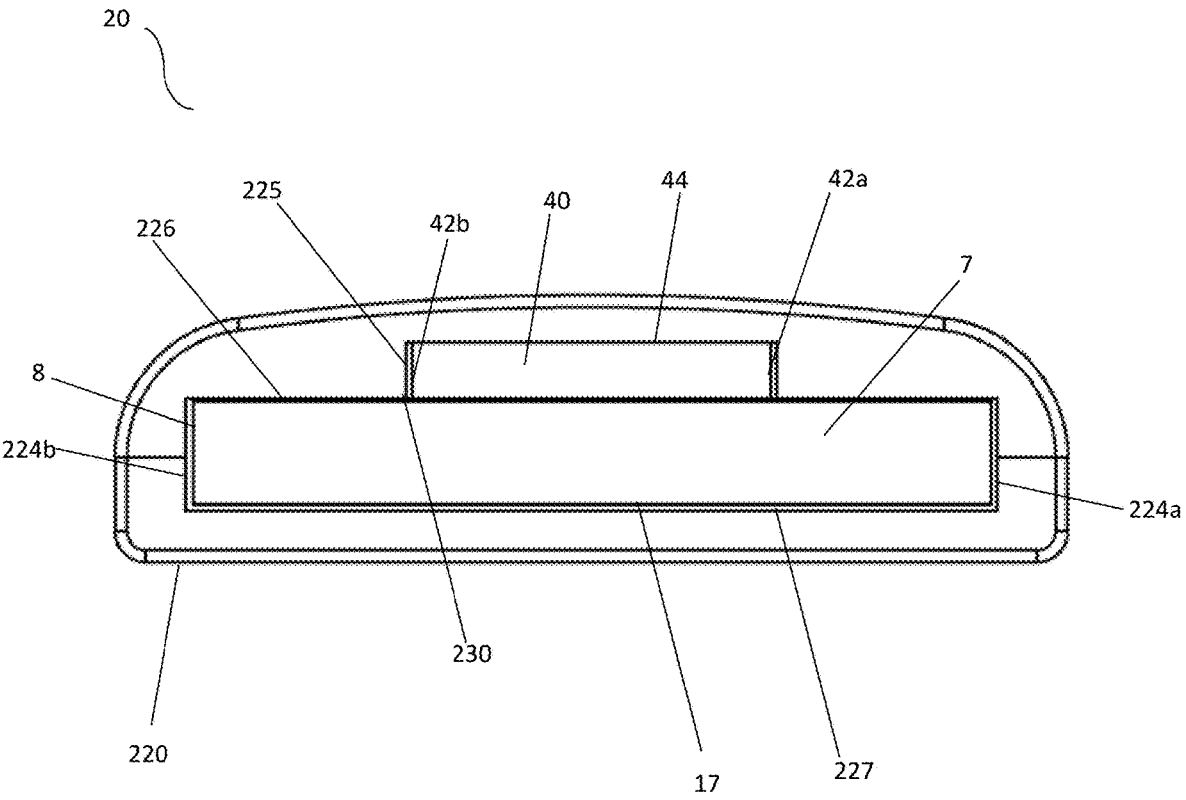
FIG. 14 is a cross-sectional view along axis C-C of FIG. 13.

FIG. 14 provides a cross-section of a housing portion 40 a secondary attachment component 200. The extension portion 7 can have a track portion 40 removably coupled, affixed, or formed to the extension portion 7. The track portion 40 can have a sidewall 42. The cavity 225 formed through the entire length of the housing member 220 can conform to the shape of the extension portion 7 and track portion 40 to ensure a secure fit with little movement when the extension portion 7 and the track portion are positioned within the cavity 225 of the housing member 220. The sidewalls 42a,b of the track portion 40 can slidably interface with a sidewall portions 224a,b of the housing or alternatively have minimal spacing from the sidewall portion to ensure little to not radial or lateral movement of the housing member on the extension portion 7.

A second sidewall portion 224b can slidably interface with a sidewall of the extension portion 8 or alternatively be minimally spaced from the sidewall 8 to further prevent lateral and radial movement of the extension portion 7 within the housing cavity. The top surface 44 of the track portion 40 can slidably interface with a surface of the interior of the cavity 225 of the housing portion 220. The cavity 220 can be near zero tolerance to ensure a snug fit of the track portion 40 and extension portion 7 within the cavity 225 to further limit or prevent the lateral and rotational movement of the extension portion 7 and track portion 40 within the cavity 225. The sidewall portions 224 of the extension portion 7 and the sidewalls of the track portion can be spaced a predetermined distance apart to form a step 230 to further limit lateral and rotational movement of the housing portion 220. The step 230 can form an additional side wall 226 to interface with a surface of the track portion 70 or extension portion 7 as shown in FIG. 14. In some exemplary embodiments, the track portion 40 can be integrated as part of the extension portion 7. In other embodiments, the track portion 40 can be removably coupled to the extension portion 7 to allow for a replaceable wear item of the track portion 40 over time if one or more of the engagement members wears down or breaks.

The width of the track portion 20 can be less than the width of the extension portion and extend upward generally perpendicular from the plane or surface of the extension portion 7. This can form the step 230 on one more sides of the track portion 20 that can be approximated by the interior cavity shape of the housing member 220. Similarly, the bottom surface 17 of the extension portion can interface with a bottom sidewall 227 of the cavity of the housing 220. The minimal tolerance and step features 230 can limit rotational and torsional movement of the extension portion 7 and track portion 40 within the housing.

In some embodiments of the design, the teeth, steps, or rungs of the track system and corresponding cuff member would be replaced by a press-fit or compression-fit mechanism, or some other means of compressing and connecting the strut member and cuff member to allow for height adjustment up and down some length of the strut while also containing a mechanism that would lock in and secure the cuff member on the strut in a multitude of positions.

Figure 15:
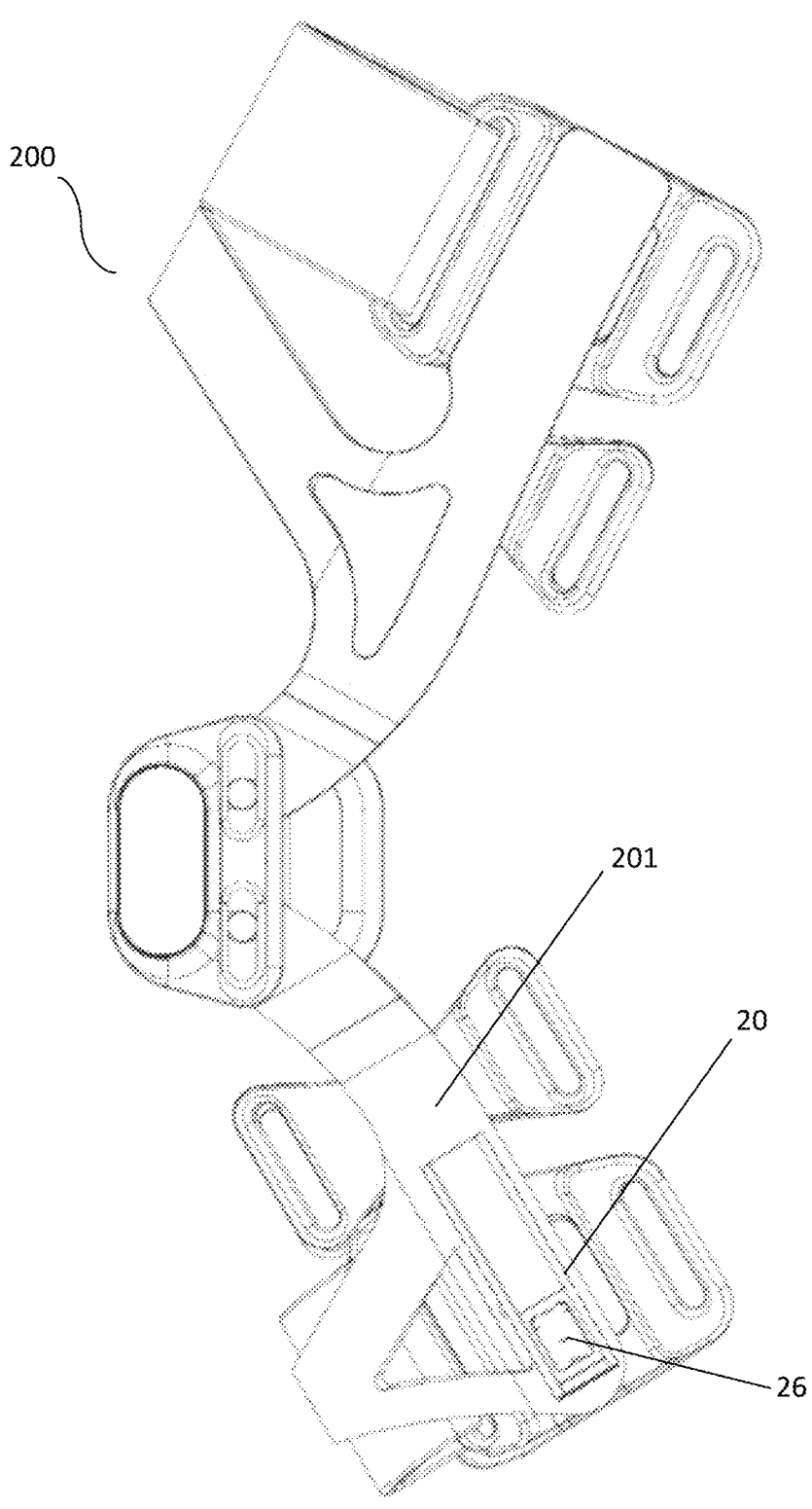
FIG. 15 is a perspective view of a knee brace further comprising an exemplary embodiment of a housing portion of the orthosis device of the present disclosure.

In other exemplary embodiments, one or more components of the present disclosure can be incorporated or coupled to additional braces to provide greater flexibility of the orthosis device depending upon the nature of a user's injury. FIG. 15 provides an illustration of a housing member 20 of the orthosis device 100 of the present coupled to a knee brace apparatus 200. The housing member 20 can be removably coupled to the additional brace apparatus 20 to allow for the other elements to be utilized in tandem with a knee brace system. The housing member 20 coupled to a brace 200 using any suitable means including one or more fasteners. Similarly, an exemplary housing member 20 of the orthosis device 100, the housing member 20 can include one or more coupling points 29 to allow for the brace 200 to be removably coupled the housing member 20. The brace 200 can have similar coupling points that can correspond to the coupling points 29 of the housing member 20. Alternatively, the housing member can be incorporated or integrated into a support portion 201 of the brace 200.

In one embodiment of this design, the housing member 20 can be designed with a slide or push button mechanism that can be utilized to lock or unlock the rungs, teeth, compression system, or steps contained within the calf cuff member to allow the cuff to slide up or down the track system or compression system on the strut and such a mechanism can be pressed, released, or otherwise engaged to lock the rungs or compression system of the cuff member with the rungs of the track system or compression system on the strut to securely hold the cuff in place at the desired height.

It should be understood that the various components of an exemplary embodiment of the orthosis device of the present disclosure can be removably couplable from each other to allow for greater flexibility and customization based upon a user's needs. In other alternative embodiments, various components can be coupled or formed together in singular structures. In some exemplary embodiments, the housing member and cuff member can be formed as a singular component. Additionally, by having removably couplable components, the various components can be replaced if they become worn down without the need to replace the entire assembly/device. This can result in increased cost savings as well as expedited repair that does not require waiting for an entirely new orthosis to be produced for a user. This can also provide the ability for a user to switch out components if they grow or change in size.

While the invention has been described above in terms of specific embodiments, it is to be understood that the invention is not limited to these disclosed embodiments. Upon reading the teachings of this disclosure many modifications and other embodiments of the invention will come to mind of those skilled in the art to which this invention pertains, and which are intended to be and are covered by both this disclosure and the appended claims. It is indeed intended that the scope of the invention should be determined by proper interpretation and construction of the appended claims and their legal equivalents, as understood by those of skill in the art relying upon the disclosure in this specification and the attached drawings.

What is claimed is:

1. An ankle foot orthosis device comprising:
a strut member having an extension portion and footplate portion, wherein the strut member includes a track portion extending along a first side of the extension portion, wherein the extension portion extends up generally perpendicular from the footplate portion;
a housing member having a cavity formed therethrough configured to house a portion of the extension portion of the strut member, wherein the housing member can move from a first position along the track portion to a second position along the track portion, wherein the track portion includes a lower stop member configured to prevent the housing member from traveling past a pre-determined distance along the extension portion, and wherein the housing member includes one or more locating apertures;
an adjustable cuff member, wherein the adjustable cuff member includes a padded portion and a fastening band; and
a locking mechanism, wherein the locking mechanism is coupled to the housing member and configured to interface with the track portion to lock the housing member at one or more positions along the track portion,
wherein the locking mechanism comprises a first surface, a second surface, a first side, second side, a third side, and a fourth side, wherein a first coupling member is formed along the first side and a second coupling member is formed along the third side, wherein the first coupling member and second coupling member are configured to interface with the housing member by approximating an edge of the housing member and wrapping around the edge of the housing member to interface with a second side of the housing member, wherein the track portion includes a plurality of engagement members configured to interface with the locking mechanism and lock the housing member at the one or more positions along the track portion, wherein the first surface of the locking mechanism further includes a first interfacing member and one or more locating members, wherein the first interfacing member is configured to interface with one or more engagement members of the plurality of engagement members and the one or more locating members is configured to interface with the one or more locating apertures.

2. The device of claim 1, further comprising a curved portion, wherein the curved portion is configured to approximate the radius of a user's ankle and connects the foot plate portion to the extension portion.

3. The device of claim 1, wherein the fastening band is configured to wrap around a first side of the housing member, exterior walls of the adjustable cuff member of the user's leg and is configured to secure the ankle foot orthosis device to the user's leg.

4. The device of claim 1, further comprising a secondary support member removably coupled to the track portion.

5. The device of claim 4, wherein the secondary support member includes a housing portion configured to be removably couplable to the track portion.

6. The device of claim 5, wherein the housing portion includes an interior cavity configured to conform to the dimensions of the extension portion and track portion to limit lateral and rotational movement of the housing portion.

7. The device of claim 6, wherein the secondary support member further includes a flange portion.

8. The device of claim 1, wherein the adjustable cuff member is capable of being incorporated into a portion of a knee brace.

* * * * *